United States Patent [19]

Buri et al.

[11] Patent Number: 5,076,846
[45] Date of Patent: Dec. 31, 1991

[54] HIGHLY CONCENTRATED AQUEOUS SUSPENSION OF MINERALS AND/OR FILLERS AND/OR PIGMENTS, STABILIZED WITH ONE OR MORE POLYAMPHOLYTES

[75] Inventors: Matthias Buri, Rothrist; Daniel Frey, Aarburg, both of Switzerland

[73] Assignee: Pluss-Staufer AG, Oftringen, Switzerland

[21] Appl. No.: 534,197

[22] Filed: Jun. 6, 1990

[30] Foreign Application Priority Data

Jun. 6, 1989 [DE] Fed. Rep. of Germany ....... 3918461
Dec. 19, 1989 [DE] Fed. Rep. of Germany ....... 3941936

[51] Int. Cl.$^5$ .............................................. C09C 3/10
[52] U.S. Cl. .................................... 106/401; 106/429; 106/447; 106/960; 106/971; 106/487; 106/499; 252/363.5; 252/351; 252/354; 252/355; 252/356; 252/357; 210/710; 210/725; 210/734; 210/735
[58] Field of Search ............... 252/363.5, 351, 354, 252/355, 356, 357, 180; 106/465, 464, 460, 446, 447, 436, 442, 487, 401, 416, 429, 471; 210/734, 735, 725, 710

[56] References Cited

U.S. PATENT DOCUMENTS

| | | | |
|---|---|---|---|
| 4,305,860 | 12/1981 | Iovine et al. | 162/164.5 |
| 4,455,240 | 6/1984 | Costello | 252/8.51 |
| 4,510,059 | 4/1985 | Amjad et al. | 252/180 |
| 4,610,801 | 9/1986 | Matthews et al. | 252/181 |
| 4,687,592 | 8/1987 | Collins et al. | 252/174.16 |
| 4,711,727 | 12/1987 | Matthews et al. | 162/164.6 |
| 4,841,040 | 6/1989 | Just et al. | 106/213 |

*Primary Examiner*—William R. Dixon, Jr.
*Assistant Examiner*—Scott L. Hertzog
*Attorney, Agent, or Firm*—Townsend and Townsend

[57] ABSTRACT

An aqueous suspension of minerals and/or fillers and/or pigments having a solid content $\geq 60\%$ by weight, the mineral or the filler or the pigment being dispersed with one or more dispersing agents, is characterized in that the dispersing agent contains one or more amphoteric polyelectrolytes and/or cationic polyelectrolytes and/or amphoteric cationoic polyelectrolytes and/or amphoteric anionic polyelectrolytes and/or partially neutralized anionic polyelectrolytes and/or partially neutralized amphoteric anionic polyelectrolytes, the filler and/or pigment and/or mineral particles carrying a charge neutral or positive to the outside.

Furthermore is disclosed a process characterized in that a part of the polyelectrolytes according to the invention is added before the grinding, a part thereof may be added during the grinding and a part thereof may be added after the grinding. According to the invention grinding and dispersing is achieved in only one process step.

35 Claims, No Drawings

HIGHLY CONCENTRATED AQUEOUS SUSPENSION OF MINERALS AND/OR FILLERS AND/OR PIGMENTS, STABILIZED WITH ONE OR MORE POLYAMPHOLYTES

The present invention relates to an aqueous suspension of minerals and/or fillers and/or pigments having a solid content ≧60% by weight with respect to the dry mineral or the dry filler or the dry pigment, the mineral or the filler or the pigment being dispersed with one or more dispersing agents.

The term "positive charges" is to be understood hereinafter to mean that the particles have a positive zeta potential at their surface (cf. P. Ney "Zeta potentials and floatability of minerals", Applied Minerology 6, Springer Publications, Vienna, N.Y., 1973, especially page 22 et seq.). This applies analogously to the "negative charges" as occur for example in cellulose fibre and anionically stabilized suspensions. For the neutral "charges", with respect to the particles, towards the outside the negative and positive charges cancel each other out. The isoelectric point need not lie at pH=7. The isoelectric point of particle surfaces and amphoteric polyelectrolytes and/or their salts, partial salts and/or full salts lies at the pH value at which the positive and negative charges neutralize each other mutually towards the outside.

Within the framework of the invention, neutral monomer units mean monomer units which do not contain any dissociable groups (for example the —COOH group), e.g. ethylene groups.

The externally, i.e. towards the outside, charged and externally neutral polyelectrolytes of the invention are defined in the present application by the number of the positive or negative groups in the polymer. Accordingly, in the amphoteric externally neutral polyelectrolytes the number of the positive charges in the cationic monomer units is equal to the number of the negative charges in the anionic monomer units. In the amphoteric cationic polyelectrolytes the non-neutral monomer units carry predominantly positive charges. In the amphoteric anionic polyelectrolytes the non-neutral monomer units carry predominantly negative charges.

This does not however mean that for example with an excess of positive charges the polyelectrolyte is automatically electrically positive. This is because the "acid strength" and the "base strength" may each be different. Thus, for example, an amphoteric polyelectrolyte having an equal number of positive and negative groups may be electrically either positive or negative or neutral. This applies correspondingly also to the amphoteric cationic polyelectrolytes and the amphoteric anionic polyelectrolytes. By displacing the pH value the dissociation of the "acid or base groups" can be influenced. In particular, at pH values between 5 and 10 the polyelectrolytes according to the invention may have the following charge states towards the outside:

| pH 5-10 | amph. polyelec. | cationic polyelec. | amph. slight. cat. polyelec. | amph. slight. an. polyelec |
|---|---|---|---|---|
| A | + neutral − | + | + neutral − | + neutral − |
| B | + = − | + | + predominant somewhat − | − predominant somewhat + |
| C | + or neutral | + | + | + or neutral |

A = possibility of the electrical charge towards the outside
B = number of charged monomer units
C = charge of the particles The neutralization of the negative groups with mono and/or bi and/or trivalent cations also influences their dissociation degree and thus the charge state towards the outside.

Anionically stabilized calcium-containing minerals such as calcium carbonate, dolomite, etc., are usually made by grinding with anionic polyacrylates, as described for example in the patents EP 0 100 947 or FR 820806. This latter patent discloses that in the case of anionically stabilized suspensions partially neutralized polyacrylic acids give better viscosity stabilities than completely neutralized acids. The disclosed range of neutralization lies between 40 and 96% neutralization; this does not lead to satisfactory results in the cationic suspension according to the invention.

It is apparent from the disclosed examples in FR 820,806 that a neutralization of <50% does not achieve the objective but that 60-70% neutralization degree represents the optimum. As described in EP 0 256 312 the minerals may also be brought into suspension with amphoteric dispersing agents. In the case of the amphoteric polyelectrolytes disclosed in this prior publication the isoelectric point lies greatly in the acidic pH range so that they are not suitable for the pigment and/or filler and/or mineral suspensions according to the invention. In addition, only amphoteric polyelectrolytes are mentioned which contain predominantly anionic monomers in their molar monomer composition. The particles according to this prior art have a negative charge on their surface.

However, for many applications the anionic stabilization is not desirable. On the contrary, it would be expedient to use a slurry with particles having a neutral or positive charge. If calcium carbonate, coated with the anionic dispersing agent, is used as filler in the paper industry it is necessary to bind the negatively charged filler with cationic retention agents to the paper fibre, which due to carboxyl groups is naturally negatively charged.

In the neutralization and flocculation of the negatively charged mineral and/or filler and/or pigment particles for the purpose of achieving the highest possible filling degrees and good filler retentions in the paper, the negatively charged paper fibre may also be flocculated and this can lead to a poorer paper formation and thereby to a more irregular transparency of the paper. With the present prior art this negative effect can hardly be avoided. For this reason, in paper production today dry-ground pulverulent products having only weakly negative or externally neutral or weakly positive surface charges are still mostly used.

However, with dry-ground products the necessary finenesses can only be achieved with very great difficulty. Furthermore, powders involve the problem of dust formation.

Cationically Stabilized Mineral and/or Filler and/or Pigment Suspensions Made by Dispersion Cationically stabilized, i.e. positively charged on the surface, partially calcium-containing minerals such as calcium carbonate, dolomite, etc., are usually prepared by dispersion in water with neutral and/or cationic protective colloids and/or cationic dispersing agents (cf. the specifications as laid open to inspection DE 3,707,221 and DE 3,730,833) or by dispersion with a combination of a fully neutralized anionic and a cationic dispersing agent, as described in European patent 0 278 602 A1, the amount of cationic polymer used in the latter being such that the particles have a positive charge in the suspension.

EP 0 278 602 also discloses polyacrylic acid. Pure non-neutralized polyacrylic acid is unsuitable because at +20° C. it already starts to crystallize and thus can no longer be dosed. Once crystallization has started the polymer solution must be heated to 100° C. to dissolve the crystals n. In winter and in colder regions production with non-neutralized polyacrylic acids is inconceivable.

These processes have the disadvantage that the comminution process, i.e. the grinding, and the dispersing must be carried out in separate steps. The following possibilities also exist in the prior art:

a) the calcium-containing rock is comminuted by dry methods to reach the necessary fineness. The fineness which can be reached in this manner is limited. Reagglomeration due to van der Waals forces largely prevent grinding to high finenesses. In a separate step, dispersion is subsequently carried out with the dispersing agents mentioned above;

b) the calcium-containing rock is ground by wet methods with low solid content (about 30% by weight) without grinding and dispersing agents and must be brought to the desired concentration via filter pressing, addition of flocculating agents or via centrifuging. In a separate step dispersion is thereafter carried out with the dispersing agents mentioned above;

c) the calcium-containing mineral is ground by wet methods with anionic dispersing agents to the desired fineness, dried and thereafter again dispersed with the aforementioned cationic polyelectrolytes and/or protective colloids. In the drying, aggregates form which cannot again be completely broken down, i.e. the resulting fineness is less than originally the case. Moreover, the anionic dispersing agent not destroyed in the drying can disturb the subsequent dispersion process and lead to an increased consumption of cationic polyelectrolyte.

In the aforementioned production processes a-c viscosity stability for longer periods of time is not obtained.

As a result, the preparation of the mineral and/or filler and/or pigment suspension must take place in the user's plant or in the immediate vicinity of the user and is spoilt in a short time due to a great viscosity rise or sedimentation. Reduction of viscosity by dilution is not possible in many cases because the high concentration is of decisive importance for the further processing, for example in coating slips or colorants in the paper industry.

Cationically Stabilized Mineral and/or Filler and/or Pigment Suspensions Produced by Grinding Recently, efforts are underway to make cationically stabilized partially calcium-containing fillers by grinding with low solid contents, as has been explained in the lecture by Loreen Goodwin, Columbia River Carbonates, held at TAPPI Papermaker, April 89 in Washington D.C.

This process has the disadvantage that the solid content is limited to 45-50% by weight. At higher concentration the viscosities are so high that the suspensions are no longer workable.

The viscosity is not stable over longer periods of time. Due to the low solid content the suspension shows a pronounced tendency to sediment and it is thus not stable in storage. The transport costs, with respect to the dry product, are about 50% more costly for 45% by weight suspensions than for 70% by weight suspensions. In addition, about 50% more storage capacity is necessary both in the manufacturing plant and in the user's plant.

In EP 0 104 904 an aqueous slurry of mineral particles having a solid content of at least 40% by weight is described. This slurry contains cationic and amphoteric polyelectrolytes with nitrogen-containing groups, although it is not apparent from the disclosure therein to the average expert what "amphoteric polyelectrolyte" means. The sole amphoteric compound mentioned is rather misleading because it does not have any apparent amphoteric character. Both DMDAAC (dimethyldiallyl ammonium chloride) and acrylamide, which were used in the copolymer referred to as amphoteric, are exclusively cationic as regards their structure.

With the aqueous slurries, sedimentation of the dispersed mineral particles within 3-7 days is accepted; this is inconceivable for transport by ship for example from Scandinavia to England, lasting 4-7 days, and would render impossible the discharge of large ships as are employed today for transports of this type.

Stirring of such large ship loads is practically impossible. For the same reasons, rail transport lasting 4-7 days in the 56 t tank trucks from Austria to North Germany is impossible. Today, both rail and ship transport is very desirable for ecological regions.

Seen from the point of view of the user, the following requirements (properties) are desirable in a suspension:

Good storability for weeks at low viscosities.

To achieve the necessary properties, for example low abrasion of the paper machine sieves in paper production and the coating doctor in the coating plant, it is necessary to produce very finely divided fillers. Also, coarse fillers in the papermaking stock show a tendency to dust in photocopying, etc.

Paper opacity, paper gloss and paper whiteness depend greatly on the fineness and the filling degrees of the fillers in and on the paper. Opacity and whiteness are of decisive importance today for the paper industry.

For the papermaking stock, today minerals and/or fillers and/or pigments are usually necessary which have an equivalent spherical diameter of the particles of 50-90% by weight <2 $\mu$m (measured with the Sedigraph 5100).

For coating compositions, today minerals and/or fillers and/or pigments are generally used having an equivalent spherical diameter of the particles up to 99% by weight <2 $\mu$m (measured with the Sedigraph 5100).

The viscosity stability must be ensured for some weeks so that the suspension is not spoilt during transport or storage by sedimentation or viscosity increase and no unnecessarily high stirring costs are incurred. For production assurance in the paper industry today, storage capacities of thousands of cubic meters of such suspensions are necessary.

The mineral and/or filler and/or pigment particles should be retainable in the paper production without using high amounts of retention aids. The strength values of the finished paper should not be greatly impaired by high filling degrees of minerals and/or pigments and/or fillers.

High filling degrees make it possible to save cellulose, this representing an enormous economical advantage for the paper industry.

Pigment and/or filler and/or mineral coating slips should penetrate as little as possible into the paper when applied thereto, remaining instead on the paper surface and thus effecting an optimum fibre coverage. A cationic coat on anionic cellulose remains considerably better on the surface.

The solid concentrations obtained should be as high as possible.

One objective of this invention is to provide storage-stable filler and/or mineral and/or pigment suspensions with high solid content and low viscosities.

This problem is solved according to the invention in that an aqueous suspension according to the preamble of claim 1 is prepared, the dispersing agent contains one or more amphoteric polyelectrolytes in which the number of the negative charges in the anionic monomer units is equal to the number of the positive charges in the cationic monomer units and which may optionally additionally contain neutral monomer units, and/or one or more cationic polyelectrolytes, and/or one or more amphoteric cationic polyelectrolytes in which the non-neutral monomer units carry predominantly positive charges, and/or one or more amphoteric anionic polyelectrolytes in which the non-neutral monomer units carry predominantly negative charges, and/or one or more partially neutralized anionic polyelectrolytes, and/or one or more partially neutralized amphoteric anionic polyelectrolytes in which the non-neutral monomer units carry predominantly negative charges, the filler and/or pigment and/or mineral particles carrying a charge neutral or positive to the outside.

A surprising and unpredictable fact was that the amphoteric polyelectrolytes according to the invention, in contrast to the prior art in which the filler and/or pigment and/or mineral particles likewise carry externally neutral or positive charges, exhibit a very good viscosity stability for a long time at low viscosities and nevertheless no sedimentation of the mineral particles takes place, even without stirring.

Hereinafter, the amphoteric polyelectrolytes in which the number of the negative charges in the anionic monomer units is equal to the number of positive charges in the cationic monomer units and the amphoteric cationic polyelectrolytes and the amphoteric anionic polyelectrolytes will be referred to briefly as amphoteric polyelectrolytes according to the invention. The amphoteric polyelectrolytes in which the number of negative charges in the anionic monomer units is equal to the number of positive charges in the cationic monomer units are referred to briefly as "amphoteric".

Within the scope of the invention it may be advantageous for some or more of the amphoteric polyelectrolytes to be partially neutralized.

Advantageously, the amphoteric anionic and the amphoteric cationic polyelectrolyte and the amphoteric polyelectrolyte in which the number of the negative charges in the anionic monomer units is equal to the number of the positive charges in the cationic monomer units carry the functional group generating the positive charge in a substituent of the ethylenic main chain.

It is further advantageous for the substituent carrying the cationic charge to be bound to the main chain via

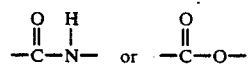

The former group is excellently suitable. It is further advantageous for the amphoteric polyelectrolytes according to the invention to contain quaternary ammonium groups, carboxyl groups and/or sulfonic acid groups and/or acidic phosphoric-ester-containing groups.

Advantageously, the amphoteric polyelectrolytes according to the invention are one or more compounds of the group of the following compounds according to the following general formula:

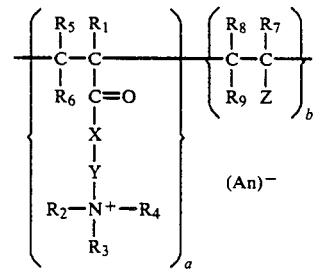

wherein $R_1$, $R_5$, $R_6$ and $R_7$ is preferably H, and/or $R_1$ to $R_7$ may be = alkyl, preferably a $C_1$-$C_{18}$-alkyl, particularly preferably $C_1$-$C_6$, optimally —$CH_3$ and/or —aryl, preferably a 6-ring, in particular a non-substituted 6-ring, $R_8$ and $R_9$ = —H and/or —alkyl, preferably a $C_1$-$C_{18}$-alkyl, particularly preferably $C_1$-$C_6$, optimally —$CH_3$ or H and/or —aryl, preferably a 6-ring, in particular a non-substituted 6-ring, and (an)$^-$ may be = chloride and/or bromide and/or iodide and/or $HSO_4^-$ and/or $CH_3SO_4^-$ and/or nitrite.

$R_8$ or $R_9$ may also be

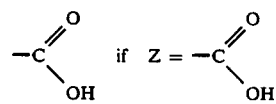

X = 0 and/or N—H
Y = —$CH_2$— to —$C_5H_{10}$—;

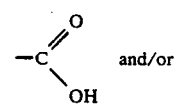

-continued

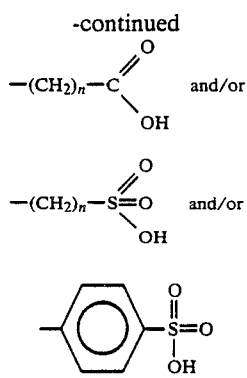

and/or may be an acidic phosphoric acid ester group and n may be =1-18. Z may be partially neutralized by 1, 2 and/or 3-valent cations.

Advantageously usable according to the invention are alkali and/or alkaline earth and/or earth metal cations, alkaline earth cations being preferred. Particularly preferred are $Ca^{++}$ and/or $Mg^{++}$ and/or $Sr^{++}$, especially preferred $Ca^{++}$ and/or $Mg^{++}$.

The neutralization degree of Z with polyvalent cations is 1 to 99 Mol. %, advantageously 50 to 98 Mol. %, preferably 70 to 97 Mol. %, and particularly preferably 95 Mol. %, in each case with respect to Z in b.

In the neutralization with monovalent cations such as $K^+$ and/or $Na^+$ and/or $Li^+$, the neutralization degree of Z is 1 to 99 Mol. %, advantageously 1 to 50 Mol. %, preferably 1 to 25 Mol. % and particularly preferably <5 Mol. %, each with respect to Z in b.

Z may also be fully neutralized when the cation is 2 and/or 3-valent or is $NH_4^+$, prim., sec., tert. amines and/or quart. ammonium ions, $NH_4^+$ leading to very unpleasant odours and possibly being injurious to health.

Z may also be present non-neutralized.

If $R_8$ or $R_9$ is not

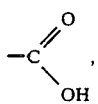

and if the amphoteric anionic polyelectrolytes are used in combination with the amphoteric cationic polyelectrolytes and the particles are thereby neutral or have positive surface charges, a and b are present in the following ratios:

| amphoteric anionic | amphoteric | amphoteric cationic |
|---|---|---|
| a = 5-49 Mol. % | a = 50 Mol. % | a = 51-99 Mol. % |
| b = 51-95 Mol. % | b = 50 Mol. % | b = 49-1 Mol. % | where n=1-18
and (an)$^-$ may be=chloride and/or bromide and/or iodide and/or $HSO_4^-$ and/or $CH_3SO_4^-$ and/or nitrite Also advantageous are the following mixtures:

| amphoteric anionic | amphoteric | amphoteric cationic |
|---|---|---|
| a = 47-49 Mol. % | a = 50 Mol. % | a = 51-80 Mol. % |
| b = 51-53 Mol. % | b = 50 Mol. % | b = 49-20 Mol. % | where
n=1-18
and (an)$^-$ may be=chloride and/or bromide and/or iodide and/or $HSO_4^-$ and/or $CH_3SO_4^-$ and/or nitrite.

If $R_8$ or $R_9$=

and if the amphoteric anionic polyelectrolytes are used in combination with the amphoteric cationic polyelectrolytes and the particles are thereby neutral or have positive surface charges, a and b are present in the following ratios:

| amphoteric anionic | amphoteric | amphoteric cationic |
|---|---|---|
| a = 10-66 Mol. % | a = 66.66 Mol. % | a = 67-99 Mol. % |
| b = 34-90 Mol. % | b = 33.33 Mol. % | b = 1-33 Mol. % | where
n=1-18
and (an)$^-$ may be=chloride and/or bromide and/or iodide and/or $HSO_4^-$ and/or $CH_3SO_4^-$ and/or nitrite.

Further advantageous are the following mixtures:

| amphoteric anionic | amphoteric | amphoteric cationic |
|---|---|---|
| a = 64-66 Mol. % | a = 66.66 Mol. % | a = 67-90 Mol. % |
| b = 34-36 Mol. % | b = 33.33 Mol. % | b = 10-33 Mol. % | where
n=1-18
and (an)$^-$ may be=chloride and/or bromide and/or iodide and/or $HSO_4^-$ and/or $CH_3SO_4^-$ and/or nitrite.

It is particularly advantageous for the amphoteric polyelectrolytes according to the invention to be a compound according to this general formula, wherein:
$R_1$=H or —$CH_3$
$R_2$=—$CH_3$ or —$C_2H_5$
$R_3$=—$CH_3$ or —$C_2H_5$
$R_4$=—$CH_3$ to —$C_4H_9$ and isomer
X=O or N—H
Y=—$CH_2$ to —$C_5H_{10}$—
$R_5$ and $R_6$=H
$R_7$=H or —$CH_3$
$R_8$ and $R_9$=H.

It is particularly advantageous if (an)$^-$=$Cl^-$ and Y=—$(CH_2)_3$—.

According to the invention, amphoteric anionic means that the anionic charges in the amphoteric polyelectrolyte are predominant with respect to the cationic charges.

Amphoteric cationic means that the cationic charges in the amphoteric polyelectrolyte are predominant with respect to the anionic charges.

Amphoteric weakly anionic or cationic means according to the invention that the corresponding negative or positive excess charges in the amphoteric polyelectrolyte are only very small. Amphoterically weak anionic means that the ratio of the anionic charge to the cationic charge lies in the range from 55:45 to 51:49 Mol. %.

Amphoteric weakly cationic means that the ratio of the anionic to the cationic charges lies in the range from 45:55 to 49:51 Mol. %.

It should be pointed out that the terms "weak" and "slight" in this application are used synonymously.

Polyelectrolytes according to the invention as defined by the following formula are particularly favourable:

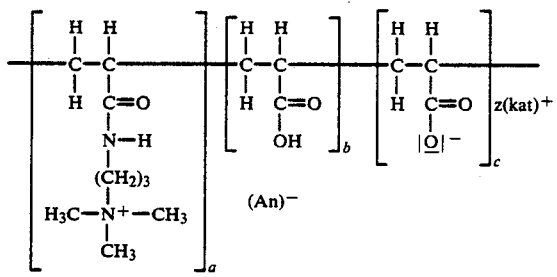

$$Z = \frac{c}{\text{Valency of } (cat)^+} \quad \text{If } c = 0, \text{ then } z = 0,$$

where $(cat)^-$ =alkali and/or alkaline earth and/or earth metal cations and/or amines and/or alkanol amines and/or quaternary ammonium cations $(an)^-$ =chloride, bromide, iodide, $HSO_4^-$, $CH_3SO_4^-$ and/or nitrite and where in the polyelectrolytes according to the invention a and b and c are present in the following ratios:

| amphoteric slightly anionic | amphoteric | amphoteric cationic |
|---|---|---|
| a = 49–47 Mol. % | a = 50 Mol. % | a = 51–80 Mol. % |
| b − c = 51–53 Mol % | b + c = 50 Mol. % | b + c = 49–20 Mol. % | where n=1–18.

Particularly advantageous are polyelectrolytes according to this general formula, where $(cat)^+$ =alkali and/or alkaline earth cations $(an)^-$ =chloride, bromide, iodide, $HSO_4^-$, $CH_3SO_4^-$ and/or nitrite and in the polyelectrolytes according to the invention a and b and c are present in the following ratios:

| amphoteric slightly anionic | amphoteric | amphoteric cationic |
|---|---|---|
| a = 49–48 Mol. % | a = 50 Mol. % | a = 51–70 Mol. % |
| b − c = 51–52 Mol. % | b + c = 50 Mol. % | b + c = 49–30 Mol. % |
| and $z = \dfrac{c}{\text{valency (cat)}^+}$ | | |

Also advantageous in the polyelectrolytes according to the invention are a and b and c in the following ratios:

| amphoteric slightly anionic | amphoteric | amphoteric cationic |
|---|---|---|
| a = 49–47 Mol. % | a = 50 Mol. % | a = 51–80 Mol. % |
| | b = 0–50 Mol. % | |
| b − c = 51–53 Mol. % | c = 50–0 Mol. % | b + c = 49–20 Mol. % |

Particularly advantageous are polyelectrolytes according to this general formula, where $(cat)^-$ =alkaline earth ions $(an)^-$ =chloride, bromide, iodide, $HSO_4^-$, $CH_3SO_4^-$ and/or nitrite and in the polyelectrolytes according to the invention a and b and c are present in the following ratios:

| amphoteric slightly anionic | amphoteric | amphoteric cationic |
|---|---|---|
| a = 49–48 Mol. % | a = 50 Mol. % | a = 51–70 Mol. % |
| | b = 0–25 Mol. % | |
| b + c = 51–52 Mol. % | c = 25–50 Mol. % | b + c = 49–30 Mol. % |
| and $z = \dfrac{c}{\text{valency (cat)}^+}$ | | |

Further advantageous are polyelectrolytes according to this general formula, where $(cat)^+$ =$Na^+$, $K^+$, $Li^+$, $Ca^{2+}$, $Mg^{2+}$, $(an)^-$ =chloride, bromide, iodide, $HSO_4^-$, $CH_3SO_4^-$ and/or nitrite and in the polyelectrolytes according to the invention a and b and c are present in the following ratios:

| amphoteric slightly anionic | amphoteric | amphoteric cationic |
|---|---|---|
| a = 49–48.5 Mol. % | a = 50 Mol. % | a = 51–60 Mol. % |
| b + c = 51–51.5 Mol. % | b + c = 50 Mol. % | b + c = 49–40 Mol. % |
| and $z = \dfrac{c}{\text{valency (cat)}^+}$ | | |

Particularly favourable results are obtained if in the polyelectrolytes according to the invention in accordance with these general formulae $(cat)^+$ =alkali cations $(an)^-$ =halide ions and in the polyelectrolytes according to the invention a and b and c are present in the following ratios:

| amphoteric slightly anionic | amphoteric | amphoteric cationic |
|---|---|---|
| a = 49 Mol. % | a = 50 Mol. % | a = 51 Mol. % |
| b = 51 Mol. % | b = 50 Mol. % | b = 49 Mol. % |
| c = <1 Mol. % | c = <1 Mol. % | c = <1 Mol. % |
| $z = \dfrac{c}{\text{valency (cat)}^+}$ | | |

Further advantageous are polyelectrolytes according to this general formula, where

| amphoteric slightly anionic | amphoteric | amphoteric cationic |
|---|---|---|
| a = 49–48.5 Mol. % | a = 50 Mol. % | a = 51–60 Mol. % |
| | b = 0–10 Mol. % | |

-continued

| amphoteric slightly anionic | amphoteric | amphoteric cationic |
|---|---|---|
| b + c = 51-51.5 Mol. % | c = 40-50 Mol. % | b + c = 49-40 Mol. % |
| and $z = \dfrac{c}{\text{valency (cat)}^+}$ | | |

Very particularly favourable results are obtained in the polyelectrolytes according to these general formulae (cat)$^+$ = alkaline earth cations
(an)$^-$ = halide ions
and in the polyelectrolytes according to the invention a and b and c are present in the following ratios:

| amphoteric slightly anionic | amphoteric | amphoteric cationic |
|---|---|---|
| a = 49 Mol. % | a = 50 Mol. % | a = 51 Mol. % |
| b = 2 Mol. % | b = 2 Mol. % | b = 2 Mol. % |
| c = 49 Mol. % | c = 48 Mol. % | c = 47 Mol. % |
| $z = \dfrac{c}{\text{valency (cat)}^+}$ | | |

Further advantageous are mixtures of amphoteric cationic polyelectrolytes and amphoteric polyelectrolytes in which the number of the cationic monomer units is equal to the number of the anionic monomer units, according to the general formula given above, where (cat)$^+$ = alkali and/or alkaline earth and/or earth metal cations and/or amines and/or alkanol amines and/or quaternary ammonium cations
(an)$^-$ = chloride, bromide, iodide, HSO$_4^-$, CH$_3$SO$_4^-$ and/or nitrite and in the polyelectrolytes according to the invention a and b and c are present in the following ratios:

| amphoteric | amphoteric cationic |
|---|---|
| a = 50 Mol. % | a = 70-99 Mol. % |
| b + c = 50 Mol. % | b + c = 30-1 Mol. % |

Further advantageous in the mixture according to the invention are the following ratios of the polyelectrolytes a and b and c in accordance with the aforementioned general formula:

| amphoteric | amphoteric cationic |
|---|---|
| a = 50 Mol. % | a = 75-98 Mol. % |
| b + c = 50 Mol. % | b + c = 25-2 Mol. % |
| preferably: | |
| a = 50 Mol. % | a = 80-97 Mol. % |
| b + c = 50 Mol. % | b + c = 20-3 Mol. % |
| further preferably: | |
| a = 50 Mol. % | a = 90-96 Mol. % |
| b + c = 50 Mol. % | b + c = 10-4 Mol. % |
| particularly preferably: | |
| a = 50 Mol. % | a = 95 Mol. % |
| b + c = 50 Mol. % | b + c = 5 Mol. % |

Further advantageous are mixtures of amphoteric slightly anionic and amphoteric cationic polyelectrolytes according to the aforementioned general formula, where (cat)$^+$ = alkali and/or alkaline earth and/or earth metal cations and/or amines and/or alkanol amines and/or quaternary ammonium cations
(an)$^-$ = chloride, bromide, iodide, HSO$_4^-$, CH$_3$SO$_4^-$ and/or nitrite and where in the polyelectrolytes according to the invention a and b and c are present in the following ratios:

| amphoteric slightly anionic | amphoteric cationic |
|---|---|
| a = 47-49 Mol. % | a = 70-99 Mol. % |
| b + c = 51-53 Mol. % | b + c = 30-1 Mol. % |
| better: | |
| a = 48-49 Mol. % | a = 75-98 Mol. % |
| b + c = 51-52 Mol. % | b + c = 25-2 Mol. % |
| preferably: | |
| a = 48.5-49 Mol. % | a = 80-97 Mol. % |
| b + c = 51-51.5 Mol. % | b + c = 20-3 Mol. % |
| particularly preferably: | |
| a = 49 Mol. % | a = 95 Mol. % |
| b + c = 51 Mol. % | b + c = 5 Mol. % |

Further advantageous are mixtures of amphoteric slightly cationic and amphoteric cationic polyelectrolytes according to the aforementioned general formula, where (cat)$^+$ = alkali and/or alkaline earth and/or earth metal cations and/or amines and or alkanol amines and/or quaternary ammonium cations
(an)$^-$ = chloride, bromide, iodide, HSO$_4^-$, CH$_3$SO$_4^-$ and/or nitrite and where in the polyelectrolytes according to the invention a and b and c are present in the following rations:

| amphoteric slightly cationic | amphoteric cationic |
|---|---|
| a = 51-53 Mol. % | a = 80-97 Mol. % |
| b + c = 49-47 Mol. % | b + c = 20-3 Mol. % |
| preferably: | |
| a = 51-52 Mol. % | a = 90-96 Mol. % |
| b + c = 49-48 Mol. % | b + c = 10-4 Mol. % |
| particularly preferably: | |
| a = 51 Mol. % | a = 95 Mol. % |
| b + c = 49 Mol. % | b + c = 5 Mol. % |

Advantageously, the neutralization degree of the anionic component in the amphoteric cationic and amphoteric weakly anionic and amphoteric weakly cationic and amphoteric polyelectrolyte with alkaline earth cations, in particular with Ca$^{++}$ and/or Mg$^{++}$, is 0.1–100 Mol. %, better 50–100 Mol. % and preferably 70–99 Mol. %, optimally 98 Mol. %, or the anionic component is non-neutralized.

Advantageously, the neutralization degree of the anionic component in the amphoteric cationic and amphoteric weakly anionic and amphoteric weakly cationic and amphoteric polyelectrolyte with monovalent cations is 0.1–100 Mol. %, better 0.1–50 Mol. % and preferably 0.1–39 Mol. % or 0.1–30 Mol. %, furthermore preferably 0.1–35 Mol. % or 0.1–25 Mol. % or 0.1–15 Mol. %, optimally <1 Mol. %, or the anionic component is non-neutralized. If 2-valent cations such as Ca$^{++}$ and Mg$^{++}$ are used, a neutralization degree of >90% is preferred. A neutralization degree of >90% with Ca$^{++}$ is better according to the invention than a neutralization degree <1% with Na$^+$.

It is advantageous for the polymerization degree of the polyelectrolytes according to the invention, measured via their viscosity in an aqueous solution at 32% concentration, to lie in the range from 5 mPa.s to 150 mPa.s. It is particularly advantageous for the viscosity to lie in the range of 15 mPa.s to 100 mPa.s, a range of 25 mPa.s to 70 mPa.s being particularly preferred.

It is further advantageous in the mixture of amphoteric cationic polyelectrolytes and amphoteric slightly cationic polyelectrolytes and/or amphoteric polyelectrolytes and/or amphoteric slightly anionic polyelectrolytes for the polymerization degree of the amphoteric cationic polyelectrolytes, measured via the limit viscosity, to lie in the range from 5 ml/g to 50 ml/g, preferably in the range from 15 ml/g to 40 ml/g, particularly preferably from 25 ml/g to 35 ml/g, and the polymerization degree of the amphoteric slightly cationic polyelectrolytes and the amphoteric polyelectrolytes and the amphoteric slightly anionic polyelectrolytes, measured via their viscosity in an aqueous solution at 32% weight concentration, to lie in the range from 5 to 150 ml/g, preferably 15 to 100 ml/g, particularly preferably from 25 to 70 ml/g.

Further advantageously, the dispersing agent contains one or more amphoteric polyelectrolytes in which the number of the negative charges in the anionic monomer units is equal to the number of the positive charges in the cationic monomer units.

Further advantageously, the dispersing agent contains a mixture of one or more amphoteric polyelectrolytes and one or more amphoteric cationic polyelectrolytes in which the non-neutral monomer units carry predominantly positive charges.

Further advantageously, the dispersing agent contains a mixture of one or more amphoteric polyelectrolytes and one or more amphoteric slightly cationic polyelectrolytes in which the non-neutral monomer units carry predominantly positive charges.

Further advantageously, the dispersing agent contains a mixture of one or more amphoteric polyelectrolytes and one or more amphoteric cationic polyelectrolytes in which the non-neutral monomer units carry predominantly positive charges and one or more amphoteric anionic polyelectrolytes in which the non-neutral monomer units carry predominantly negative charges.

Further advantageously, the dispersing agent contains a mixture of one or more amphoteric polyelectrolytes and one or more amphoteric slightly cationic polyelectrolytes in which the non-neutral monomer units carry predominantly positive charges and one or more amphoteric anionic polyelectrolytes in which the non-neutral monomer units carry predominantly negative charges.

Further advantageously, the dispersing agent contains a mixture of one or more amphoteric polyelectrolytes and one or more amphoteric cationic polyelectrolytes in which the non-neutral monomer units carry predominantly positive charges and one or more amphoteric slightly anionic polyelectrolytes in which the non-neutral monomer units carry predominantly negative charges.

Further advantageously, the dispersing agent contains a mixture of one or more amphoteric polyelectrolytes and one or more amphoteric slightly cationic polyelectrolytes in which the non-neutral monomer units carry predominantly positive charges and one or more amphoteric slightly anionic polyelectrolytes in which the non-neutral monomer units carry predominantly negative charges.

Further advantageously, the dispersing agent contains one or more amphoteric cationic polyelectrolytes in which the non-neutral monomer units carry predominantly positive charges.

Further advantageously, the dispersing agent contains one or more amphoteric cationic polyelectrolytes and one or more amphoteric slightly cationic polyelectrolytes in which the non-neutral monomer units carry predominantly positive charges.

Further advantageously, the dispersing agent contains one or more amphoteric slightly cationic polyelectrolytes in which the non-neutral monomer units carry predominantly positive charges.

Further advantageously, the dispersing agent contains a mixture of one or more amphoteric cationic polyelectrolytes in which the non-neutral monomer units carry predominantly positive charges and one or more amphoteric anionic polyelectrolytes in which the non-neutral monomer units carry predominantly negative charges.

Further advantageously, the dispersing agent contains a mixture of one or more amphoteric slightly cationic polyelectrolytes in which the non-neutral monomer units carry predominantly positive charges and one or more amphoteric anionic polyelectrolytes in which the non-neutral monomer units carry predominantly negative charges.

Further advantageously, the dispersing agent contains a mixture of one or more amphoteric cationic polyelectrolytes in which the non-neutral monomer units carry predominantly positive charges and one or more amphoteric slightly anionic polyelectrolytes in which the non-neutral monomer units carry predominantly negative charges.

Further advantageously, the dispersing agent contains a mixture of one or more amphoteric slightly cationic polyelectrolytes in which the non-neutral monomer units carry predominantly positive charges and one or more amphoteric slightly anionic polyelectrolytes in which the non-neutral monomer units carry predominantly negative charges.

Further advantageously, the dispersing agent contains a mixture of one or more amphoteric polyelectrolytes and one or more amphoteric slightly anionic polyelectrolytes in which the non-neutral monomer units carry predominantly negative charges.

Further advantageously, the dispersing agent contains one or more amphoteric slightly anionic polyelectrolytes in which the non-neutral monomer units carry predominantly negative charges.

When using the amphoteric slightly anionic polyelectrolytes, in spite of the slight excess of negative charge (carboxyl groups) the filler particles have a neutral or slightly positive surface charge. This is probably due to part of the carboxyl groups being neutralized by $Ca^{++}$ ions to such an extent that they are no longer present dissociated and thus act neutral to the outside. Consequently, the dissociated cationic groups predominate and the filler particles do not have a negative charge in spite of carboxyl group excess in the actual dispersing agent.

This is particularly the case with a ratio of 51–53 Mol. % carboxyl groups to 47–49 Mol. % quaternary ammonium groups in the polymer molecule.

Further preferred is a ratio of 51 to 52 Mol. % carboxyl groups to 49–48 Mol. % quaternary ammonium groups in the polymer molecule. Particularly preferred is a ratio of 51 Mol. % carboxyl groups to 49 Mol. % quaternary ammonium groups in the polymer molecule.

Preferably, the dispersing agent contains 0 to 100% by weight of a first amphoteric polyelectrolyte and 100–0% by weight of a second amphoteric polyelectrolyte.

Further preferably, the dispersing agent contains a mixture of 0.1 to 99.9% by weight of one or more amphoteric polyelectrolytes and 99.9 to 0.1% by weight of one or more amphoteric cationic polyelectrolytes.

Particularly preferably, the dispersing agent contains a mixture of 50–99.9% by weight or 80 to 99 9% by weight or 10–50% by weight or 10–30% by weight of one or more amphoteric polyelectrolytes and 0.1 to 50% by weight or 0.1 to 20% by weight or 50–90% by weight or 70–90% by weight of one or more amphoteric cationic polyelectrolytes.

Further preferably, the dispersing agent contains 0.1 to 99.9% by weight of one or more amphoteric polyelectrolytes and 99.9 to 0.1% by weight of one or more amphoteric slightly cationic polyelectrolytes.

Further preferably, the dispersing agent contains a mixture of 0.1 to 99.8% by weight of one or more amphoteric polyelectrolytes and 0.1 to 99.8% by weight of one or more amphoteric cationic polyelectrolytes and 0.1 to 99.8% by weight of one or more amphoteric anionic polyelectrolytes.

Further preferably, the dispersing agent contains a mixture of 0.1 to 20% by weight of one or more amphoteric polyelectrolytes and 60 to 79.9% by weight of one or more amphoteric cationic polyelectrolytes and 0.1 to 20% by weight of one or more amphoteric anionic polyelectrolytes.

Further preferably, the dispersing agent contains a mixture of 0.1 to 99.8% by weight of one or more amphoteric polyelectrolytes and 0.1 to 99.8% by weight of one or more amphoteric slightly cationic polyelectrolytes and 0.1 to 99.8% by weight of one or more amphoteric anionic polyelectrolytes.

Further preferably, the dispersing agent contains a mixture of 0.1 to 99.8% by weight of one or more amphoteric polyelectrolytes and 0.1 to 99.8% by weight of one or more amphoteric cationic polyelectrolytes and 0.1 to 99.8% by weight of one or more amphoteric slightly anionic polyelectrolytes.

Further preferably, the dispersing agent contains a mixture of 0.1 to 99.8% by weight of one or more amphoteric polyelectrolytes and 0.1 to 99.8% by weight of one or more amphoteric slightly cationic polyelectrolytes and 0.1 to 99.8% by weight of one or more amphoteric slightly anionic polyelectrolytes.

Further preferably, the dispersing agent contains 0 to 100% by weight of a first amphoteric cationic polyelectrolyte and 0 to 100% by weight of a second amphoteric cationic polyelectrolyte.

Further preferably, the dispersing agent contains 0.1 to 9.9% by weight of a first amphoteric slightly cationic polyelectrolyte and 0.1 to 99.9% by weight of a second amphoteric slightly cationic polyelectrolyte.

Further preferably, the dispersing agent contains 50 to 9.9% b weight or 70 to 99.9% by weight of one or more amphoteric cationic polyelectrolytes and 0.1 to 50% by weight or 0.1 to 30% by weight of one or more amphoteric anionic polyelectrolytes.

Further preferably, the dispersing agent contains a mixture of 90 to 99.9% by weight or 75 to 90% by weight or 80% by weight of one or more amphoteric cationic polyelectrolytes and 0.1 to 10% by weight or 25 to 10% by weight or 20% by weight of one or more amphoteric anionic polyelectrolytes.

Further preferably, the dispersing agent contains a mixture of 80 to 99.9% by weight of one or more amphoteric slightly cationic polyelectrolytes and 0.1 to 20% by weight of one or more amphoteric anionic polyelectrolytes.

Further preferably, the dispersing agent contains a mixture of 0.1 to 99.9% by weight of one or more amphoteric cationic polyelectrolytes and 99.9 to 0.1% by weight of one or more amphoteric slightly anionic polyelectrolytes.

Further preferably, the dispersing agent contains 50 to 9.9% by weight or 70 to 90% by weight or 75% by weight of one or more amphoteric cationic polyelectrolytes and 0.1 to 50% by weight or 10 to 30% by weight or 25% by weight of one or more amphoteric slightly anionic polyelectrolytes.

Further preferably, the dispersing agent contains 0.1 to 9.9% by weight of one or more amphoteric slightly cationic polyelectrolytes and 99.9 to 0.1% by weight of one or more amphoteric slightly anionic polyelectrolytes Further preferably, the dispersing agent contains a mixture of 0.1 to 99.9% by weight or 50 to 99.9% by weight of one or more amphoteric polyelectrolytes and 0.1 to 99.9% by weight or 0.1 to 50% by weight of one or more amphoteric slightly anionic polyelectrolytes.

Further preferably, the dispersing agent contains 0 to 100% by weight of a first and 0 to 100% by weight of a second amphoteric slightly anionic polyelectrolyte.

According to the invention, the minerals or fillers or pigments include in particular elements of the second and/or third main group and/or fourth subgroup of the periodic system of the elements. Favourably, calcium-containing and/or silicon-containing and/or aluminium-containing and/or titanium-containing minerals and/or fillers and/or pigments are used, calcium-carbonate-containing minerals and/or fillers and/or pigments being preferred. Very particularly preferred are natural calcium carbonate and/or precipitated calcium carbonate and/or marble and/or chalk and/or dolomite and/or dolomite-containing calcium carbonate.

The aqueous suspension preferably consists of 97.0% by weight to 99.97% by weight minerals and/or fillers and/or pigments and water and 0.03% by weight–3.0% by weight of the amphoteric polyelectrolytes according to the invention with a solid content of 60–80% by weight, with respect to dry mineral or the dry filler or the dry pigment.

It is further favourable for the aqueous suspension to consist of 98.5 to 99.95% by weight minerals and/or fillers and/or pigments and water and 0.05 to 1.5% by weight of the amphoteric polyelectrolytes according to the invention with a solid content of 65–77% by weight with respect to the dry mineral or the dry filler or the dry pigment.

Furthermore, good results are obtained if the aqueous suspension consists of 98.8 to 99.90% by weight minerals and/or fillers and/or pigments and water and 0.1% by weight to 1.2% by weight of the amphoteric polyelectrolytes according to the invention with a solid content of 67–76% by weight with respect to the dry mineral or the dry filler or the dry pigment.

Excellent results are obtained if the aqueous suspension consists of 99.5% by weight or 98.8% by weight or 99.6% by weight minerals and/or fillers and/or pigments and water and 0.5% by weight or 1.2% by weight or 0.4% by weight of an amphoteric externally neutral polyelectrolyte having a viscosity of 37 mPa.s with a solid content of 72% by weight or 72% by weight or 67% by weight, with respect to the dry mineral or the dry filler or the dry pigment, with a grain distribution such that 70% by weight or 90% by weight or 60% by weight of the particles have an equivalent spherical diameter <2 μm.

It is further advantageous for the aqueous suspension to consist of 97 to 99.89% by weight, better 98.5 to 99.8% by weight, better 99.2 to 99.65% by weight minerals and/or fillers and/or pigments and water and a dispersing agent mixture of amphoteric cationic and amphoteric slightly anionic and/or amphoteric and/or amphoteric slightly cationic polyelectrolytes in the range from 0.11 to 3.00% by weight, better 0.2 to 1.5% by weight, better 0.35 to 0.8% by weight, each with respect to a solid content in the range of 60-80 by weight, preferably 62-75% by weight, particularly 65-72% by weight with respect to the dry mineral or the dry filler or the dry pigment.

Excellent results are achieved if the aqueous suspension consists of 99.6% by weight minerals and/or fillers and/or pigments and water and 0.4% by weight of the dispersing agent mixture set forth above according to the invention.

Particularly good results are achieved if the aqueous suspension consists of 99.6% by weight minerals and/or fillers and/or pigments and water and 0.4% by weight of a dispersing agent mixture consisting of 0.35% by weight of an amphoteric cationic polyelectrolyte according to the general formula on page 17, wherein a=95 Mol. % and b=5 Mol. % and c=0 Mol. % for a limit viscosity of 27.3 ml/g and 0.1% by weight of an amphoteric polyelectrolyte according to the general formula on page 17, wherein a=50 Mol. % and b=50 Mol. % and c=0 Mol. %, having a viscosity, measured in an aqueous solution of 32% by weight, of 37 mPa.s with a solid content of 67% by weight, 60% by weight of the particles having an equivalent spherical diameter <2 μm.

A further objective of the invention is to provide a process with which a storage-stable highly concentrated mineral and/or filler and/or pigment suspension can be prepared by grinding with high solid contents, grinding and dispersing taking place with high solid contents in one working operation.

This objective is achieved according to the invention in that a process for preparing an aqueous suspension is provided which is characterized by the following process steps:

a) an aqueous suspension of minerals and/or fillers and/or pigments is wet ground together with a dispersing and grinding agent mixture according to the invention, b) the amphoteric polyelectrolytes according to the invention being added completely before the grinding or c) a part of the amphoteric polyelectrolytes according to the invention being added before the grinding and d) a part of the amphoteric polyelectrolytes according to the invention being added during the grinding and/or e) a part of the amphoteric polyelectrolytes according to the invention being added after the grinding.

A process is particularly advantageous wherein a) the amphoteric slightly anionic and/or the amphoteric polyelectrolytes are added completely before the grinding or b) a part of the amphoteric slightly anionic and/or of the amphoteric polyelectrolytes is added before the grinding and c) a part of the amphoteric slightly anionic and/or of the amphoteric polyelectrolytes is added during the grinding and/or d) a part of the amphoteric slightly anionic and/or of the amphoteric polyelectrolytes are added after the grinding.

Also advantageous is a process wherein a) the amphoteric and/or the amphoteric cationic polyelectrolytes are added completely before the grinding or b) a part of the amphoteric and/or of the amphoteric cationic polyelectrolytes are added before the grinding and c) a part of the amphoteric and/or of the amphoteric cationic polyelectrolytes is added during the grinding and/or d) a part of the amphoteric and/or of the amphoteric cationic polyelectrolytes is added after the grinding.

Particularly advantageous is a process wherein a) 50-100% by weight of the amphoteric slightly anionic and/or of the amphoteric polyelectrolytes are added before the grinding and b) 0-50% by weight of the amphoteric slightly anionic and/or of the amphoteric polyelectrolytes is added during the grinding and/or c) 0-50% by weight of the amphoteric slightly anionic and/or of the amphoteric polyelectrolytes is added after the grinding.

Also advantageous is a process wherein a) 50-100% by weight of the amphoteric and/or of the amphoteric cationic polyelectrolytes is added before the grinding and b) 0-50% by weight of the amphoteric and/or of the amphoteric cationic polyelectrolytes is added during the grinding and/or c) 0-50% by weight of the amphoteric and/or of the amphoteric cationic polyelectrolytes is added after the grinding.

Very good results are achieved if a process is employed wherein a) 70-100% by weight of the amphoteric slightly anionic and/or of the amphoteric polyelectrolytes is added before the grinding and/or b) 0-30% by weight of the amphoteric slightly anionic and/or of the amphoteric polyelectrolytes is added during the grinding and/or c) 0-30% by weight of the amphoteric slightly anionic and/or of the amphoteric polyelectrolytes is added after the grinding.

Also advantageous is a process wherein a) 70-100% by weight of the amphoteric and/or of the amphoteric cationic polyelectrolytes is added before the grinding and b) 0-30% by weight of the amphoteric and/or of the amphoteric cationic polyelectrolytes is added during the grinding and/or c) 0-30% by weight of the amphoteric and/or of the amphoteric cationic polyelectrolytes is added after the grinding.

Also advantageous is a process wherein a) a part of the amphoteric slightly cationic and/or of the amphoteric and/or of the amphoteric slightly anionic polyelectrolytes is added before the grinding and b) a part of the amphoteric slightly cationic and/or of the amphoteric and/or of the amphoteric slightly anionic polyelectrolytes is added during the grinding and/or c) a part of the amphoteric slightly cationic and/or of the amphoteric and/or of the amphoteric slightly anionic polyelectrolytes is added after the grinding.

Also advantageous is a process wherein a) the amphoteric cationic polyelectrolytes are completely added before the grinding or b) a part of the amphoteric cationic polyelectrolytes is added before the grinding and c) a part of the amphoteric cationic polyelectrolyte is added during the grinding and/or d) a part of the amphoteric cationic polyelectrolytes is added after the grinding.

Particularly advantageous is a process wherein a) 10-90% by weight or 20-40% by weight or 30% by weight of the amphoteric slightly cationic and/or of the amphoteric and/or of the amphoteric slightly anionic polyelectrolytes is added before the grinding and b) 10-90% by weight or 60-80% by weight or 70% by weight of the amphoteric slightly cationic and/or of the amphoteric and/or of the amphoteric slightly anionic polyelectrolytes is added during the grinding and/or c) 0-80% by weight or 0-20% by weight of the amphoteric slightly cationic and/or amphoteric and/or amphoteric slightly anionic polyelectrolytes is added after the grinding.

Particularly preferred is a process wherein a) 50-100% by weight or 70-100% by weight of the amphoteric cationic polyelectrolytes is added before the grinding and 0-50% by weight or 0-30% by weight of the amphoteric cationic polyelectrolytes is added during the grinding and/or c) 0-50% by weight or 0-30% by weight of the amphoteric cationic polyelectrolytes is added after the grinding.

Excellent results are obtained with the process in which on the one hand 100% by weight of the amphoteric slightly anionic and/or the amphoteric polyelectrolytes or on the other hand 100% by weight of the amphoteric and/or the amphoteric cationic polyelectrolytes are added before the grinding if the desired end fineness is to be achieved in one mill passage.

When several mill passages are needed to achieve the end fineness excellent results are obtained if the necessary dispersing agent amount is divided up corresponding to the intermediate fineness achieved.

According to the invention, the aqueous suspension of minerals and/or fillers and/or pigments is used paper manufacture or paper production. Further uses are the surface treatment (pigmenting) of the paper surface in the size press of the papermaking machine, the use in the paper coating plant, in the preliminary coat or in the top coat in paper coating, in wood pulp for impurity control (pitch control), in the circulation water of the papermaking machine for COD reduction (chemical oxygen demand reduction), in the purification plant for waste water treatment, for preflocculating anionically stabilized pigment and/or mineral and/or filler suspensions in paper production or for preflocculating (immobilization) of coating slips in the coating apparatus.

The invention has succeeded in preparing a mineral and/or filler and/or pigment suspension by grinding with high solid contents of >60% by weight in which the mineral and/or filler and/or pigment particles are stabilized presumably both electrostatically positively as well as sterically and the suspension remains adequately stable as regards viscosity for weeks, can be transported very well over long distances, does not sediment and for example the retention in paper production is excellent.

A surprising and unpredictable effect was that with the suitable combinations of one or more cationic monomers and one or more anionic monomers and the suitable addition point of the resulting polymerized amphoteric polyelectrolytes before, and/or during and/or after the grinding process, under the high shearing forces and temperature which occur in wet grinding no mutual neutralization of the oppositely charged monomer units and thus coagulation of the polymers occurs. On the contrary, optimum grinding and stabilizing of the suspension over long periods of time is achieved.

The zeta potentials of the filler and/or pigment and/or mineral particles have a positive sign or are externally neutral, i.e. in the neutral filler and/or pigment and/or mineral particles the sum totals of the positive and negative charges on the surface of the particles cancel each other out towards the outside.

A particularly good storability with respect to the viscosity and the sedimentation behaviour is of decisive importance in particular in transport and in the case of large storage tanks to prevent the material being spoilt. With the mineral and/or filler and/or pigment suspension made according to the invention it is possible to choose freely the production location (manufacturing location of the mineral and/or filler and/or pigment suspension) and the use location (e.g. paper mill). The production location can thus be adapted to the geological occurrence of the mineral and/or filler and/or pigment materials and there is no need to take account of the location of the customer for purely logistical reasons. Also, there is complete freedom of choice in the means of transport and the ecologically best option can be selected.

An aqueous suspension of minerals and/or fillers and/or pigments having a solid content $\geq 60\%$ by weight with respect to the dry minerals and/or fillers and/or pigments, is prepared according to the invention by grinding a coarsely broken crude rock, the amphoteric polyelectrolytes according to the invention being added at the start of the grinding and/or further parts of the amphoteric polyelectrolytes according to the invention being added during the grinding and/or after the grinding, each in the composition according to the invention, to reduce the viscosity.

According to the process of the invention the grain distribution, concentration and storability at low viscosity of the mineral and/or filler and/or pigment suspension ideal for the user, mainly the paper industry, may be achieved in one working operation, representing an enormous economic and qualitative advance.

Preferably, the concentration of the aqueous slurry is 60-78% by weight with respect to the dry mineral.

Preferably the raw material before the grinding process according to the invention has a mean equivalent spherical particle diameter of 10-50 $\mu$m (measured on the Sedigraph 5100).

Preliminary notes to the examples:

a) Viscosity measurement of the amphoteric polyelectrolytes

The viscosity measurement was carried out with a Brookfield Viscometer Type PVF-100 at 100 rpm. For the individual measurements, the spindle 1 was employed:

For all samples the concentration was 32% by weight polymer in water. The pH value at which the viscosity was measured corresponds to the value indicated in the corresponding examples. The anionic groups were not neutralized.

The measurement was carried out in a 400 ml beaker of low form.

The temperature during the measurement was 20° C. and the measurement was made after 1 min. stirring time.

This type of viscosity measurement was employed for all the following examples with the exception of the amphoteric cationic polyelectrolytes in the mixture with the amphoteric slighly cationic and/or amphoteric and/or amphoteric slightly anionic polyelectrolytes.

b) Fineness of the mineral and/or filler and/or pigment suspension

The fineness characteristics of the suspensions prepared according to the invention were determined by sedimentation analysis under gravity with the SEDIGRAPH 5100 of the company Micromeritics, U.S.A.

The measurement of the cationically stabilized suspensions was carried out in distilled water. The dispersion of the samples was carried out by means of high-speed agitators and ultrasonic vibrations.

The measurement of the powders was carried out in 0.1% $Na_4P_2O_7$ solution.

The particle distribution measured was represented on an X-Y plotter as passage sum curve (see for example Belger, P., Schweizerische Vereinigung der Lack- und Farben-Chemiker, XVII. FATIPEC Congress, Lugano, September 23 to 28, 1984), the particle diameter of a corresponding spherical diameter being plotted along the X axis and the proportion of particles in % by weight being plotted along the Y axis.

c) Viscosity measurement of the mineral and/or filler and/or pigment suspension:

The viscosity measurement was carried out on a Brookfield Viscometer Type PVF-100 at 100 rpm. The following spindles were employed for the individual measurements:

| Spindle | | |
|---|---|---|
| RV 2 | 40–320 | mPas |
| RV 3 | 320–800 | mPas |
| RV 4 | 800–1600 | mPas |
| RV 5 | 1600–3200 | mPas |
| RV 6 | 3200–8000 | mPas |

The measurement was carried out in a 400 ml beaker of low form.

The temperature during the measurement was 20° C. The measurement was carried out after 1 min. stirring time.

Before the actual measurements all the samples were intensively agitated for 2 min. (5000 rpm, agitating blade diameter 50 mm).

This type of viscosity measurement was employed for all the following examples.

d) The specific viscosity for the anionic dispersing agent in the use examples which bears as symbol the Greek letter "Eta" was determined as follows:

A solution of the polymer/copolymer is made, 100% neutralized with sodium hydroxide solution (pH 9) for the measurement, by dissolving 50 g, with respect to the dry polymer/copolymer, in 1 lt, 60 g NaCl-containing distilled water.

Thereafter, with a capillary viscometer with a Baume constant of 0.000105 in a heating bath thermostabilized at 25° C. the time is measured which an exactly defined volume of the alkaline polymer/copolymer solution requires to flow through the capillary and compared with the time which the same volume of the dummy solution with 60 g NaCl/l needs to flow through the capillary.

It is thus possible to define the specific viscosity "Eta" as follows:

$$Eta = \frac{\text{Time of passage of the polymer solution} - \text{Time of passage of the NaCl solution}}{\text{Time of passage of the NaCl solution}}$$

The best results are obtained if the capillary diameter is chosen so that the time required by the polymer/copolymer-containing NaCl solution requires is between 90 and 100 sec.

e) The limit viscosity of the amphoteric cationic polyelectrolytes in the mixture with the amphoteric slightly cationic and/or amphoteric and/or amphoteric slightly anionic polyelectrolytes and of poly-DADMAC or examples 1a) to 1c) was determined in accordance with the following literature:

B. Vollmert "Outlines of macromolecular chemistry", volume III

E. Vollmert-Verlag, Karlsruhe 1985.

f) Charge measurement of the pigment, filler and mineral suspension with SCD To determine the surface charges the "Streaming Current Detector" of the company Muetek, Herrsching near Munich, was used (Type PCD-02).

The titrations were carried out in accordance with the observations in the dissertation "Investigations on the use of polyelectrolyte titration in the field of paper manufacture" by Peter Hess, Darmstadt, 1983, in particular in accordance with pages 33 et seq. of this dissertation.

As standard titrating solution 0.01M potassium polyvinyl sulfate solution (PPVS) of the company SERVA was employed.

PRODUCTION EXAMPLES

I. Examples from the Prior Art

Example 1a

A 60% by weight aqueous slurry of natural marble with a grain distribution such that 60% by weight of the particles have an equivalent spherical diameter <2 μm (measured on the Sedigraph 5100) was dispersed with 0.1% by weight of a poly(diallyldimethyl ammonium chloride), limit viscosity 25 ml/g, and 0.02% by weight of a sodium polyacrylate (specific viscosity 0.35, 100% of the carboxyl groups neutralized with NaOH), in each case with respect to the dry marble, under strong shearing forces (8000 rpm, agitator blades φ 50 mm).

| Viscosity in mPas | | | |
|---|---|---|---|
| after 1 hour | 2 days | 6 days | 12 days |
| 204 | 420 | 640 | 1560 |

Example 1a shows that the viscosity in the prior art is not stable and that the suspension is already useless after two weeks.

Example 1b

An attempt was made to grind a 67% by weight aqueous slurry of natural marble with an equivalent spherical mean particle diameter of 12 μm (measured on the Sedigraph 5100) in accordance with the following recipe on a Dynomill (0.6 l grinding container) using grinding bodies of glass (φ 1 mm) to a grain distribution curve such that 60% by weight of the particles have an equivalent spherical diameter <2 μm (measured on the Sedigraph 5100).

| Recipe: | |
|---|---|
| 5000 g | marble |
| 15 g | poly(diallyldimethyl ammonium chloride) limit viscosity 25 ml/g |
| 4.5 g | sodium polyacrylate (spec. viscosity 0.35, 100% of the carboxyl groups neutralized with NaOH) |
| 2472 g | water |

The grinding had to be stopped because the viscosity rise was so great that further grinding was no longer possible because the mill was blocked. It was not possible to reach the desired end fineness.

EXAMPLE 1c

A 60% by weight aqueous slurry of natural marble having an equivalent spherical mean particle diameter of 12 μm (measure on the Sedigraph 5100) was ground on a Dynomill (0.6 l grinding container) using grinding bodies of glass (φ 1 mm) to a grain distribution curve such that 60% by weight of the particles had an equivalent spherical diameter <2 μm (measured on the Sedigraph 5100).

| Recipe: | |
|---|---|
| 5000 g | marble |
| 15 g | poly(diallyldimethyl ammonium chloride) limit viscosity 25 ml/g |
| 4.5 g | sodium polyacrylate (spec. viscosity 0.35, 100% of the carboxyl groups neutralized with NaOH) |
| 3346 g | water |

Even with a concentration of 60% by weight there was no improvement in the grinding properties with a poly(diallyldiemthyl ammonium chloride) compared with test 1b.

With the prior art grinding to the desired fineness was not possible with viscosities <2000 mPas.

II. Examples According to the Invention

Example 2

A 67% by weight aqueous slurry of natural marble with a grain distribution such that 60% by weight of the particles have an equivalent spherical diameter <2 μm (measured on the Sedigraph 5100) was prepared with different amounts, with respect to the dry marble, of the following copolymer:

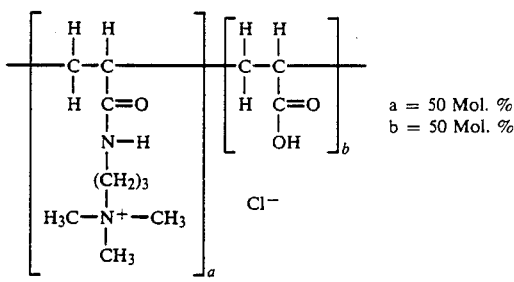

the copolymer being additionally varied in molecular weight or intrinsic viscosity of the 32% by weight aqueous solution. Dispersion was carried out under vigorous stirring (8000 rpm, agitator blade diameter 50 mm).

The objective of this series of tests was to determine the optimum viscosity and the molecular weight of the amphoteric polyelectrolytes as well as the optimum amount of dispersing agent.

TABLE 1

| Viscosity and pH value of the amphoteric polyelectrolyte (32% by weight in H₂O) viscosity pH value | Amount added in % by weight with respect to the dry marble | Viscosity of the suspension | |
|---|---|---|---|
| | | immediately | after 20 days |
| 95 mPas 3.3 | 0.1 | 1440 | |
| | 0.15 | 840 | |
| | 0.2 | 610 | |
| | 0.25 | 420 | |
| | 0.30 | 340 | |
| | 0.35 | 275 | |
| | 0.4 | 215 | |
| | 0.5 | 165 | 155 |
| 61 mPas 3.3 | 0.1 | 1430 | |
| | 0.2 | 420 | |
| | 0.3 | 265 | |
| | 0.4 | 190 | 180 |
| 37 mPas 3.3 | 0.1 | 950 | |
| | 0.2 | 250 | |
| | 0.3 | 145 | 230 |
| 24 mPas 3.5 | 0.1 | 1910 | |
| | 0.2 | 1180 | |
| | 0.3 | 670 | |
| | 0.4 | 455 | |
| | 0.5 | 360 | |
| | 0.6 | 275 | |
| | 0.7 | 200 | 280 |

The optimum viscosity of the amphoteric polyelectrolyte is 30–50 mPas.

Example 3

A 67% by weight aqueous slurry of natural marble having a grain distribution such that 60% by weight of the particles have an equivalent spherical diameter <2 μm (measured on the Sedigraph 5100) was prepared with different amounts, with respect to the dry marble, of the following copolymer:

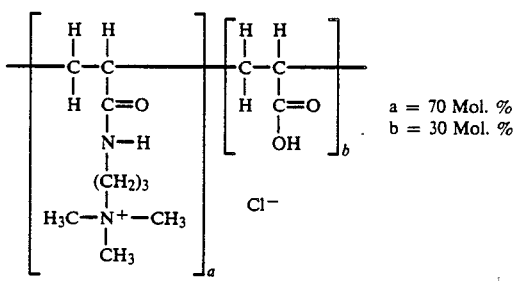

a = 70 Mol. %
b = 30 Mol. % the copolymer being additionally varied in molecular weight or intrinsic viscosity of the 32% by weight aqueous solution. Dispersion was carried out under vigorous stirring (8000 rpm, agitator blade diameter 50 mm).

The objective of this series of tests was to determine the optimum viscosity and the molecular weight of the amphoteric cationic polyelectrolytes as well as the optimum amount of dispersing agent.

TABLE 2

| Viscosity and pH value of the amphoteric cationic polyelectrolyte (32% by weight in H₂O) viscosity pH value | Amount added in % by weight with respect to the dry marble | Viscosity of the suspension | |
|---|---|---|---|
| | | immediately | after 10 days |
| 106 mPas 3.7 | 0.1 | 465 | |
| | 0.2 | 260 | |
| | 0.3 | 200 | 345 |
| 44 mPas 3.7 | 0.1 | 535 | |
| | 0.2 | 220 | |
| | 0.3 | 140 | 375 |
| 33 mPas 3.7 | 0.1 | 1090 | |
| | 0.2 | 750 | |
| | 0.3 | 570 | |
| | 0.4 | 430 | |
| | 0.5 | 290 | |
| | 0.6 | 200 | 530 |

Example 4

A 67% by weight aqueous slurry of natural marble having a grain distribution such that 60% by weight of the particles have an equivalent spherical diameter of <2 μm (measured on the Sedigraph 5100) was prepared with different amounts, with respect to the dry marble, of the following copolymer:

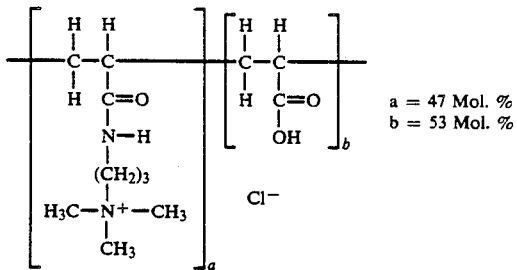

a = 47 Mol. %
b = 53 Mol. % the copolymer being additionally varied in molecular weight or intrinsic viscosity of the 32% by weight aqueous solution. Dispersion was carried out under vigorous stirring (8000 rpm, agitation blade diameter 50 mm).

The objective of this series of tests was to determine the optimum viscosity and the molecular weight of the amphoteric slightly anionic polyelectrolytes as well as the optimum amount of dispersing agent.

TABLE 3

| Viscosity and pH value of the amphoteric slightly anionic polyelectrolyte (32% by weight in H₂O) viscosity pH value | Amount added in % by weight with respect to the dry marble | Viscosity of the suspension | |
|---|---|---|---|
| | | immediately | after 10 days |
| 84 mPas 3.1 | 0.1 | 1500 | |
| | 0.2 | 840 | |
| | 0.3 | 420 | |
| | 0.4 | 275 | |
| | 0.5 | 185 | 165 |
| 40 mPas 3.0 | 0.1 | 1180 | |
| | 0.2 | 265 | |
| | 0.3 | 165 | 190 |

Example 5

A 72% by weight aqueous slurry of natural marble having an equivalent spherical mean particle diameter of 12 μm (measured no the Sedigraph 5100) was ground in accordance with the following recipe on a Dynomill (0.6 l grinding container) using grinding bodies of glass (φ 1 mm) to a grain distribution curve such that 70% by weight of the particles had an equivalent spherical diameter <2 μm (measured on the Sedigraph 5100).

Recipe:
```
   5000 g     marble
     25 g     amphoteric copolymer
              corresponding to the formula of
              example 2 (viscosity 37 mPas)
   1925 g     water
```
Viscosity: after 2 hours  1 day  5 days  8 days  16 days
               215         255    300     365     430
           after 30 days
               515          mPas
Surface charge after 7 days + 7.9 μVal/g solid.

It is clearly apparent in Example 5 that with the use according to the invention of the amphoteric polyelectrolytes according to the invention at high concentrations a very low viscosity adequately stable for weeks is achieved even with finely divided mineral and/or filler and/or pigment suspensions produced by grinding.

Example 6

A 72% by weight aqueous slurry of Champagne chalk having an equivalent spherical mean particle diameter of 12 μm (measured on the Sedigraph 5100) was ground in accordance with the following recipe on a Dynomill (0.6 l grinding container) using grinding bodies of glass (φ 1 mm) to a grain distribution curve such that 90% by weight of the particles had an equivalent spherical diameter <2 μm (measured on the Sedigraph 5100).

Recipe:
```
   5000 g     Champagne chalk
     60 g     amphoteric copolymer
              from example 2
              (viscosity 37 mPas)
   1715 g     water.
```
Viscosity in mPas:  after 1 hr  1 day  10 days  20 days
                       600      650     710      900

Example 7

A 72% by weight aqueous slurry of natural marble having an equivalent spherical mean particle diameter of 12 μm (measured on the Sedigraph 5100) was ground in accordance with the following recipe on a Dynomill (0.6 l grinding container) using grinding bodies of glass (φ 1 mm) to a grain distribution curve such that 90% by weight of the particles had an equivalent spherical diameter <2 μm (measured on the Sedigraph 5100).

Recipe:
  5000 g   marble
    55 g   amphoteric polymer from example 2
  1418 g   water.

| Viscosity in mPas: | after 1 hr | 1 day | 10 days | 20 days |
|---|---|---|---|---|
|  | 740 | 780 | 870 | 980 |

Surface charge after 7 days + 10.1 μVal/g solid.

Example 7a

In pilot-plant scale the marble used in Example 7 was ground in a vertically arranged Permill (Sussmeier with 180 liter content) with grinding bodies of glass (φ 1–2 mm) to a grain distribution curve such that 90% by weight of the particles had an equivalent spherical diameter <2 μm (measured on the Sedigraph 5100) with a concentration of 74.5% by weight. About 2 tonnes of this slurry were made.

Recipe:
  1480 kg   marble
   10.4 kg  amphoteric polymer from example 2
    510 kg  water added

| Viscosity in mPas: | after 1 hr | 1 day | 10 days | 20 days |
|---|---|---|---|---|
|  | 600 | 560 |  | 680 |

Surface charge after 7 days + 11.9 μVal/g solid.

Examples 6, 7 and 7a show that even very high finenesses as are used in coating recipes can be made in high concentrations without any problems by grinding coarsely broken crude rock.

Example 8

A 67% by weight aqueous slurry of natural marble having an equivalent spherical mean particle diameter of 12 μm (measured on the Sedigraph 5100) was ground in accordance with the following recipe in a Dynomill (0.6 l grinding container) using grinding bodies of glass (φ 1 mm) to a grain distribution curve such that 60% by weight of the particles had an equivalent spherical diameter <2 μm (measured on the Sedigraph 5100).

Recipe:
  5000 g   marble
    20 g   amphoteric copolymer corresponding to the formula of example 2 (viscosity 37 mPas)
  2472 g   water added

| Viscosity in mPas: | after 2 hrs. | 1 day | 5 days | 8 days | 16 days |
|---|---|---|---|---|---|
|  | 120 | 130 | 140 | 212 | 208 |
|  | 30 days |  |  |  |  |
|  | 520 |  |  |  |  |

Surface charge after 7 days + 4.8 μVal/g solid.

In example 8 it is clearly apparent that with the use according to the invention of amphoteric externally neutral polyelectrolytes at high concentrations a very low viscosity sufficiently stable for weeks is achieved even with fine mineral and/or filler and/or pigment suspensions made by grinding, as are used as filler for paper manufacture.

Example 9

A 72% by weight aqueous slurry of natural marble having an equivalent spherical mean particle diameter of 12 μm (measured on the Sedigraph 5100) was ground in accordance with the following recipe in a Dynomill (0.6 l grinding container) using grinding bodies of glass (φ 1 mm) to a grain distribution curve such that 60% by weight of the particles had an equivalent spherical diameter <2 μm (measured on the Sedigraph 5100).

Recipe:
  5000 g   marble
    25 g   amphoteric polymer from example 5, in (a) 95 Mol. % of the carboxyl groups being neutralized with Ca(OH)$_2$ and in (b) 95 Mol. % being neutralized with Mg(OH)$_2$.
  2460 g   water added.

| Viscosity in mPas: | after 1 hr. | 1 day | 4 days | 8 days | 16 days |
|---|---|---|---|---|---|
| (a) | 96 | 110 | 130 | 140 | 160 |
| (b) | 104 |  |  |  | 155 |

Example 9 shows that the calcium and/or magnesium neutralization according to the invention of the carboxyl groups in the amphoteric polyelectrolyte, in spite of a considerably higher solid content and only slightly more dispersing agent than in example 8, gives a still better viscosity than the same unneutralized amphoteric polyelectrolyte.

Example 10

A 67% by weight aqueous slurry of natural marble having an equivalent spherical mean particle diameter of 12 μm (measured on the Sedigraph 5100) was ground in accordance with the following recipe in a Dynomill (0.6 l grinding container) using grinding bodies of glass (o 1 mm) to a grain distribution curve such that 60% by weight of the particles had an equivalent spherical diameter <2 μm (measured on the Sedigraph 5100).

Recipe:

5000 g marble
17.5 g amphoteric cationic copolymer of the following formula:

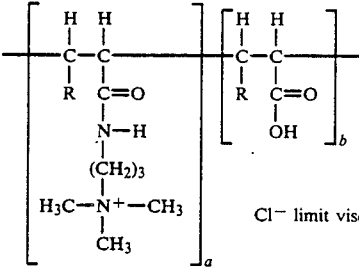

2.5 g amphoteric copolymer, the anionic and cationic groups being present in the ratio 1:1 analogously to example 2 with a viscosity of 37 mPas, added before the grinding
2.5 g "like the first 2.5 g" added during the grinding
2472 g water.

| Viscosity: after | 2 hrs. | 1 day | 4 days | 8 days | 16 days |
|---|---|---|---|---|---|
|  | 450 cP | 450 cP | 520 cP | 615 cP | 730 cP |
|  | 30 days |  |  |  |  |
|  | 830 cP |  |  |  |  |

Example 10 shows that with the combination according to the invention of the amphoteric polyelectrolytes according to the invention a transportable non-sedimenting slurry of calcium carbonate can be made by grinding coarsely broken rock. The viscosity at high concentration is good.

The marble slurries made in production examples 5+8 were investigated for their retention in papermaking in comparison with a marble slurry made today usually with anionic dispersing agents.

| Test conditions: | | |
|---|---|---|
| Material: | 80% birch sulfate 20% pine sulfate | grinding degree 23°SR |
| Retention aid: | | 0.05% polyacrylamide (limit viscosity 700 ml/g) |

Execution of the retention investigation according to Britt-jar, company Paper Research Material, SYRACUSE, U.S.A.:

1. 275 mlg 2% fibre suspension (OD 3.63 g fibres) and 275 ml dist. water introduced into the Britt-jar;
2. Britt-jar agitator at 700 rpm;
3. add 25.4 ml 5% mineral and/or filler and/or pigment suspension;
4. after 20 sec. add corresponding amount of retention agent:
5. after a further 25 sec. open drain cock and allow 100 ml backwater to run off.
6. In the backwater the $CaCO_3$ content is determined complexometrically after digestion with HCl or by flame AAS. For other minerals and/or fillers and/or pigments the backwater is filtered via membrane filters, ashed at 600° C., brought via an alkaline melt digestion, for example with NaOH/KOH in a zirconium crucible, to a water-soluble form and determined by means of AAS in the acidified state. By taking account of the corresponding convertion factors the respective minerals and/or fillers and/or pigments can be deduced.
7. Via the incorporated amount of minerals and/or fillers and/or pigments per 100 ml and the amount of minerals and/or fillers and/or pigments per 100 ml determined in the backwater, the filler retention can be calculated.

| Results: | |
|---|---|
| Products: | Filler First-pass retention |
| Anionically stabilized $CaCO_3$ suspension with 60% < 2 μm (0.15% sodium polyacrylate spec. visc. 0.35) | 41.1% |
| anionically stabilized $CaCO_3$ suspension with 70% < 2 μm (0.3% sodium polyacrylate spec. viscosity 0.54) | 35.3% |
| $CaCO_3$ suspension from preparation example 8 | 62.4% |
| $CaCo_3$ suspension from preparation example 5 | 65.8% |

By using a marble suspension produced with the new preparation method according to the invention it is possible to increase the filler retention without impairing the paper formation and paper strength, representing an enormous advance in the development.

The aqueous suspensions according to the invention and the process according to the invention for their preparation have among others the following advantages:

In contrast to the processes known hitherto it is possible to prepare highly concentrated (>60% by weight) mineral and/or filler and/or pigment suspension by wet grinding from coarsely broken crude rock.

It is possible to increase the filler without appreciable decrease of the tearing strength of the paper giving an enormous economical advantage in paper production. It was further found with the composition according to the invention that it is possible to increase the filling degree from 15% by weight to 17% by weight without any appreciable loss of paper strength, in particular tearing strength.

Very recent practical tests have shown that a filler increase from 16% to 26% can be achieved without impairing the paper properties.

The suspensions have excellent storage stability with low viscosities without any sedimentation problems.

In use there are for example great advantages with regard to filler retention in paper production.

The grinding and dispersion is possible under high grinding forces and at the boiling temperature of the water.

The ecologically optimum transport facility can be chosen.

A preferable embodiment of the invention is characterized in that the dispersing agent is a mixture of one or more cationic polyelectrolytes and/or one or more amphoteric cationic polyelectrolytes in which the non-neutral monomer units carry predominantly positive charges, and one or more partially neutralized anionic polyelectrolytes and/or one or more partially neutralized amphoteric anionic polyelectrolytes in which the non-neutral monomer units carry predominantly negative charges.

Hereinafter the partially neutralized anionic or cationic polyelectrolytes and the partially neutralized amphoteric anionic or cationic polyelectrolytes will be briefly designated anionic polyelectrolytes according to the invention or cationic polyelectrolytes according to the invention.

Advantageously, the dispersing agent is a mixture of one or more homopolymeric cationic polyelectrolytes and/or one or more copolymeric amphoteric cationic polyelectrolytes in which the non-neutral monomer units carry predominantly positive charges, and one or more homo and/or copolymeric partially neutralized anionic polyelectrolytes and/or one or more amphoteric anionic partially neutralized polyelectrolytes in which the non-neutral monomer units carry predominantly negative charges.

Advantageously, the cationic polyelectrolyte and/or amphoteric cationic polyelectrolyte in which the non-neutral monomer units carry predominantly positive charges carries the functional group generating the positive charge in a substituent of the ethylenic main chain.

It is further advantageous for the substituent to be bound to the main chain via

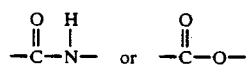

Also advantageous is that the cationic polyelectrolyte contains quaternary ammonium groups and the amphoteric cationic polyelectrolyte in which the non-neutral monomer units carry predominantly positive charges contains quaternary ammonium groups and carboxyl groups and/or sulfonic acid groups and/or acidic phosphoric-acid-ester-containing groups.

It is particularly advantageous for the cationic polyelectrolyte to be one or more compounds of the group of the following compounds according to the following general formula:

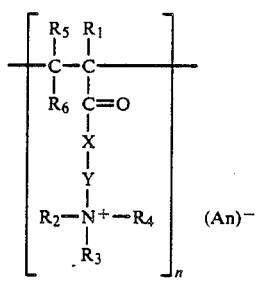

where
$R_1$, $R_5$ and $R_6$ = —H and/or $R_1$ to $R_6$ = alkyl and/or —aryl,
and $R_5$ may also be

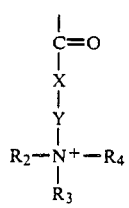

$X = O$ and/or $N$—$H$
$Y = $ —$CH_2$ to —$C_5H_{10}$—
$n = 20$ to 3000
and $(An)^- = $ chloride and/or bromide and/or iodide and/or $HSO_4^-$ and/or $CH_3SO_4^-$ and/or nitrite.

It is particularly advantageous if in accordance with this general formula
$R_1 = H$ or —$CH_3$
$R_2 = $ —$CH_3$ or —$C_2H_5$
$R_3 $ —$CH_3$ or —$C_2H_5$
$R_4 = $ —$CH$ to —$C_4H_9$ and isomer
$X = O$ or $N$—$H$
$Y = $ —$CH_2$ to —$C_5H_{10}$,
$R_5$ and $R_6 = H$,
in particular if $Y = $ —$(CH_2)_3$— and $X = $ —$NH$.

Advantageously the amphoteric cationic polyelectrolyte in which the non-neutral monomer units carry predominantly positive charges is one or more compounds of the group of the following compounds according to the following general formula

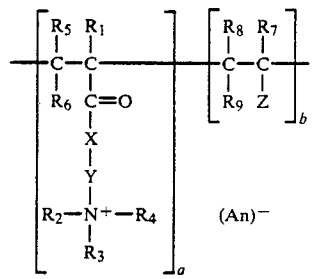

where
$R_1$, $R_5$, $R_6$ and $R_7 = H$ and/or $R_1$ to $R_7 = $ alkyl and/or —aryl,
and $R_5$ may also be

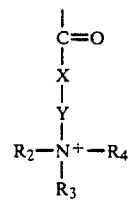

$R_8$ and $R_9$ may be = —H and/or —alkyl and/or —aryl;
$R_8$ or $R_9$ may be

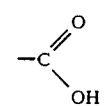

when $Z = $ 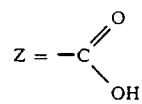

$X = O$ and/or $N$—$H$
$Y = $ —$CH_2$ to —$C_5H_{10}$—

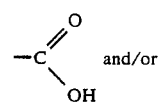 and/or

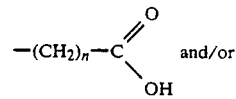 and/or

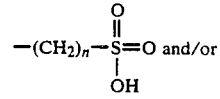 and/or

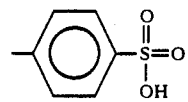

and/or an acidic phosphoric acid ester group,
a = 70–99 Mol. %
b = 1–30 Mol. % n=1–18 and (An)⁻ =chloride and/or bromide and/or iodide and/or HSO₄⁻ and/or CH₃SO₄⁻ and/or nitrite.

It is particularly advantageous for the amphoteric cationic polyelectrolyte to be a compound according to this general formula, where
$R_1$=H or —CH₃
$R_2$=—CH₃ or —C₂H₅
$R_3$=—CH₃ or —C₂H₅
$R_4$=—CH₃ to —C₄H₉ and isomer
X=O or N—H
Y=—CH₂— to —C₅H₁₀—,
$R_5$ and $R_6$=H
$R_7$=H or —CH₃
$R_8$ and $R_9$=H.

It is very particularly advantageous if (an)⁻=Cl⁻ and Y=—(CH₂)₃—.

It is further advantageous if the anionic partially neutralized polyelectrolyte is one or more compounds of the group of the following compounds according to the following general formula

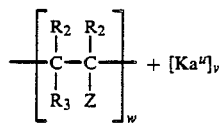

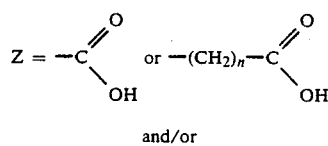

and/or

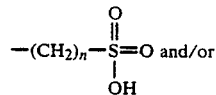

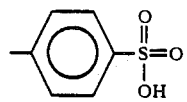

and/or an acidic phosphoric acid ester group
$R_1$=—H or —CH₃
$R_2$ and $R_3$=—H and/or —alkyl and/or —aryl
and where $R_2$ or $R_3$ may also be Z when

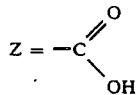

u=+I and/or +II and/or +III
Ka=alkaline and/or alkaline earth and/or earth metal ion
w=59 to 95 Mol. % per number Z in monomer
v=5 to 41 Mol. % divided by u
n=1–12.

It is further advantageous for the partially neutralized anionic polyelectrolyte to be a mixture of one or more of the homo and/or copolymers of compounds according to this general formula.

Also advantageous is that the amphoteric anionic partially neutralized polyelectrolyte in which the non-neutral monomer units carry predominantly negative charges is one or more compounds of the group of the compounds according to the following general formula:

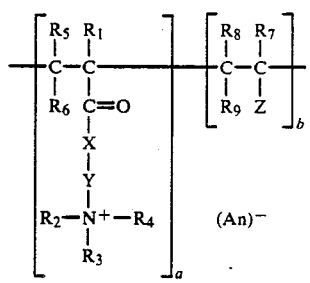

where
$R_1$, $R_5$, $R_6$ and $R_7$=H —and/or $R_1$ to $R_7$ —alkyl and/or —aryl,
and $R_5$ may also be

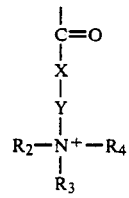

$R_8$ and $R_9$ may also be=—H and/or —alkyl and/or —aryl;
$R_8$ or $R_9$ may also be

if

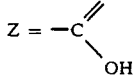

X=O and/or N—H
Y=—CH₂ to —C₅H₁₀—

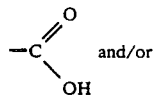 and/or

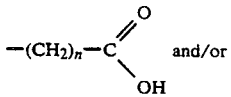 and/or

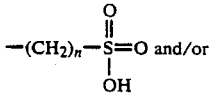 and/or

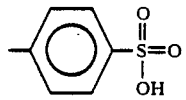

and/or may be an acidic phosphoric acid ester group.

a=1-30 Mol. %
b=70-99 Mol. %
n=1-18 and (an)⁻=chloride and/or bromide and/or iodide and/or HSO₄⁻ and/or CH₃SO₄⁻ and/or nitrite.

It is particularly advantageous for the amphoteric anionic partially neutralized polyelectrolyte to be one or more compounds according to this general formula, where $R_1$ = H or —CH₃
$R_2$ = —CH₃ or —C₂H₅
$R_3$ = —CH₃ or —C₂H₅
$R_4$ = —CH₃ to —C₄H₉ and isomer
X = O or N—H
Y = —CH₂— to —C₅H₁₀—,
$R_5$ and $R_6$ = H
$R_7$ = H or —CH₃
$R_8$ and $R_9$ = H.

It is very particularly advantageous if (an)⁻=Cl⁻ and Y=—(CH₂)₃—.

A further favourable embodiment of the invention is that the anionic partially neutralized polyelectrolyte is a homo and/or copolymer. and that the amphoteric anionic partially neutralized polyelectrolyte in which the non-neutral monomer units carry predominantly negative charges is a polyelectrolyte containing carboxyl groups and/or sulfonic acid groups and/or, acidic phosphoric acid ester groups.

In particular, advantageously the partially neutralized anionic polyelectrolyte is a partially neutralized polyacrylic acid and/or a partially neutralized polymethacrylic acid and/or a partially neutralized copolymer thereof.

Advantageously, in the anionic partially neutralized polyelectrolyte and in the amphoteric anionic partially neutralized polyelectrolyte only a statistical part of the acid groups is neutralized with a mono and/or multivalent cation.

Conveniently, as cations alkali and/or alkaline earth and/or earth metal cations and/or amines and/or alkanol amines and/or quaternary ammonium cations are used, it being particularly advantageous to use as cations Na⁺ and/or K⁺ and/or Li⁺ and/or NH₄⁺ and/or Ca²⁺ and/or Mg²⁺ and/or Sr²⁺. Very particularly good results are obtained if as cations alkali and/or alkaline earth cations are used, in particular alkali cations and here in particular Na⁺. NH₄⁺ is particularly unsuitable because it leads to unpleasant odours and is injurious to health.

Dispersing agents which are particularly suitable according to the invention are mixtures according to the general formulae of claim 14 and/or of the amphoteric cationic polyelectrolytes of claim 15 and of claim 16 and/or of the amphoteric anionic partially neutralized polyelectrolytes of claim 15.

Particularly favourable is a dispersing agent mixture according to the following general formula:

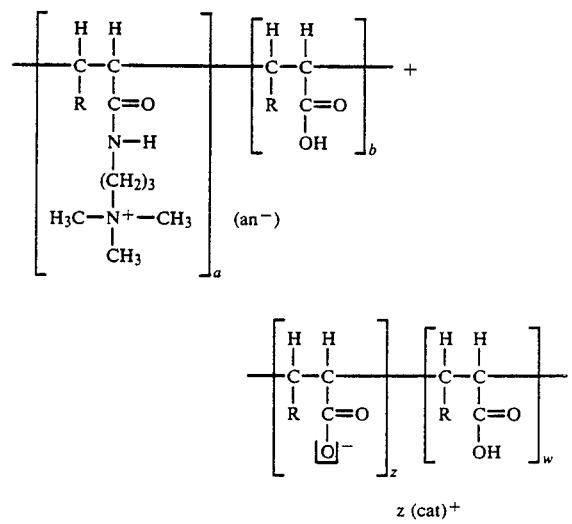

where (cat)⁺ = alkali and/or alkaline earth and/or earth metal ions and/or amines and/or alkanol amines and/or quaternary ammonium cations (an)⁻ = chloride, bromide, iodide, HSO₄⁻, CH₃SO₄⁻ and/or nitrite.

a = 60-99 Mol. %
b = 1-40 Mol. %
z = 1-70 Mol. %
w = 30-99 Mol. %.

Particularly advantageous are dispersing agent mixtures according to this general formula, where (cat)⁺ = alkali and/or alkaline earth ions
(an)⁻ = chloride and/or bromide and/or iodide and/or HSO₄⁻ and/or CH₃SO₄⁻ and/or nitrite and a = 80-98 Mol. %
b = 2-20 Mol. %
z = 2-50 Mol. %
w = 50-98 Mol. %.

Also advantageous are dispersing agent mixtures according to this general formula, where (cat)⁺ = Na⁺ and/or K⁺ and/or Li⁺ and/or Ca²⁺ and/or Mg²⁺ and/or Sr²⁺

(an)⁻ = chloride and/or bromide and/or iodide and/or HSO₄⁻ and/or CH₃SO₄⁻ and/or nitrite, and a = 85-97 Mol. %
b = 3-15 Mol. %
z = 3-30 Mol. %
w = 70-97 Mol. %.

Very particularly favourable results are obtained if the dispersing agent mixture is a mixture of this general formula, where (cat)⁺ = alkali ion
(an)⁻ = halogen ion
a = 90-96 Mol. %
b = 4-10 Mol. %
z = 4-20 Mol. %
w = 80-96 Mol. %

Excellent results are obtained if the dispersing agent mixture is a mixture according to this general formula, where (cat)⁺ = Na⁺
(an)⁻ = Cl⁻
a = 95 Mol. %
b = 5 Mol. %
z = 5 Mol. % w=95 Mol. %,

Advantageously, the anionic polyelectrolyte and/or the amphoteric anionic polyelectrolyte are partially neutralized with alkali and/or alkaline earth and/or earth metal cations and/or amines and/or alkanol amines and/or quaternary ammonium cations, and in particular alkali and/or alkaline earth cations are suitable, quite particularly alkali cations and here especially Na+ cations.

Conveniently, in the anionic polyelectrolytes and/or in the amphoteric anionic polyelectrolytes 1 to 70 Mol. % of the acid groups are neutralized. Particularly favourable results are achieved if 2 to 60 Mol. %, in particular 3 to 30 Mol. %, of the acid groups are neutralized, a neutralization degree of 5 Mol. % to 10 Mol. % giving the best results.

Non-neutralized polyacrylic acid is not suitable because it already starts to crystallize at +20° C. and is thus no longer dosable. Once crystallization has started, the polymer solution must be heated to 100° C. to dissolve the crystals again. In winter and in colder regions production with non-neutralized polyacrylic acids is inconceivable.

Advantageously, the specific viscosity "Eta" of the partially neutralized anionic polyelectrolyte and/or of the amphoteric anionic polyelectrolyte in the mixture with the cationic and/or the amphoteric cationic polyelectrolyte, measured in the full salt form, lies between 0.2 and 1.0. It is particularly advantageous if "Eta" lies between 0.35 and 0.6 and it is very particularly favourable if "Eta" is 0.55.

Advantageously, the polymerization degree of the cationic polyelectrolyte and/or of the amphoteric cationic polyelectrolyte in the mixture with the partially neutralized anionic polyelectrolyte and/or the amphoteric anionic partially neutralized polyelectrolyte, measured via the limiting viscosity, lies in the range from 5 ml/g to 50 ml/g. Very particularly advantageous is a polymerization degree in the range of 15 ml/g to 40 ml/g, a range of 25 ml/g to 35 ml/g being particularly preferred.

Advantageously, the dispersing agent mixture consists of 70–98% by weight cationic polyelectrolyte and/or amphoteric cationic polyelectrolyte and 2–30% by weight anionic partially neutralized polyelectrolyte and/or amphoteric partially neutralized anionic polyelectrolyte.

It is further advantageous for a dispersing agent mixture to consist of

75–95% by weight cationic polyelectrolyte according to the invention and 5–25% by weight of the anionic polyelectrolyte according to the invention. Further advantageous are dispersing agent mixtures of 80–90% by weight of the cationic polyelectrolytes according to the invention and 10 to 20% by weight of the anionic polyelectrolytes according to the invention. Very particularly advantageous are dispersing agent mixtures of 80 or 90% by weight of the cationic polyelectrolytes according to the invention and 20 or 10% by weight of the anionic polyelectrolytes according to the invention.

Advantageously, the mixture ratio of cationic polyelectrolyte to amphoteric cationic polyelectrolyte in the mixture with the partially neutralized anionic and/or the partially neutralized amphoteric anionic polyelectrolyte is 0–100% by weight cationic polyelectrolyte and 100–0% by weight amphoteric cationic polyelectrolyte. Also preferred is a mixture ratio of 0 to 30% by weight cationic polyelectrolyte and 70 to 100% by weight amphoteric cationic polyelectrolyte, in particular a mixture ratio of 0 to 20% by weight cationic polyelectrolyte and 80 to 100% by weight amphoteric cationic polyelectrolyte.

Preferably, the molar composition of the individual components in the partially neutralized anionic polyelectrolyte in the mixture with the cationic and/or amphoteric cationic polyelectrolyte lies between 0 Mol. % and 100 Mol. % acrylic acid and 100 Mol. % to 0 Mol. % other monomers. Expediently, the other monomers contain carboxyl groups and/or sulfonic acid groups and/or acidic phosphoric acid ester groups.

It is particularly favourable for the molar composition of the individual components in the partially neutralized anionic amphoteric polyelectrolyte in the mixture with the cationic and/or amphoteric cationic polyelectrolyte to lie between 0 Mol. % to 99 Mol. % acrylic acid and 100 Mol. % to Mol. % other monomers.

Very particularly favourable results are achieved if the other monomers contain carboxyl groups and/or sulfonic acid groups and/or acidic phosphoric acid ester groups and/or one or more compound from the group of compounds according to the general formula of claim 14.

It is very particularly advantageous if the anionic polyelectrolyte is partially neutralized acrylic acid. Advantageously, 2–80 Mol. % of the acid groups of the anionic polyelectrolyte are neutralized, particularly advantageously 3 to 70 Mol. % and very particularly advantageously 3 to 10 Mol. % of the acid groups.

According to the invention the minerals or fillers or pigments contain in particular elements of the second and/or third main group and/or of the fourth subgroup of the periodic system of the elements. Expediently, calcium-containing and/or silicon-containing and/or aluminium-containing and/or titanium-containing minerals and/or fillers and/or pigments are used, calcium carbonate-containing minerals and/or fillers and/or pigments being preferred. Quite particularly preferred are natural calcium carbonate and/or precipitated calcium carbonate and/or marble and/or chalk and/or dolomite-containing calcium carbonate.

The aqueous suspension consists preferably of 97.0 to 99.89% by weight minerals and/or fillers and/or pigments and water and 0.11% by weight–3.0% by weight of a mixture of cationic and/or amphoteric cationic and partially neutralized anionic and/or partially neutralized amphoteric anionic polyelectrolyte with a solid content of 60–80% by weight with respect to the dry mineral or the dry filler or the dry pigment.

Also favourable is that the aqueous suspension consists of 98.5 to 99.8% by weight minerals and/or fillers and/or pigments and water and 0.2% by weight–1.5% by weight of a mixture of cationic and/or amphoteric cationic and partially neutralized anionic and/or partially neutralized amphoteric anionic polyelectrolyte with a solid content of 60–75% by weight with respect to the dry mineral or the dry filler or the dry pigment.

Furthermore, good results are achieved if the aqueous suspension consists of 99.2% by weight to 99.65% by weight minerals and/or fillers and/or pigments and water and 0.35% by weight–0.8 weight of a mixture of cationic and/or amphoteric cationic and partially neutralized anionic and/or partially neutralized amphoteric anionic polyelectrolyte with a solid content of 60–70% by weight with respect to the dry mineral or the dry filler or the dry pigment.

Excellent results are achieved if the aqueous suspension consists of 99.6% by weight or 99.05% by weight or 99.1% by weight minerals and/or fillers and/or pigments and water and 0.4% by weight or 0.95% by weight or 0.9% by weight of a mixture of cationic and-/or amphoteric cationic and partially neutralized anionic and/or partially neutralized amphoteric anionic polyelectrolyte, with a solid content of 67% by weight or 67% by weight or 60% by weight with respect to the dry mineral or the dry filler or the dry pigment with a grain distribution such that 60% by weight or 70% by weight or 90% by weight of the particles have an equivalent spherical diameter <2 μm.

Advantageously, the anionic polyelectrolyte and/or amphoteric anionic polyelectrolyte in the mixture with the cationic and/or amphoteric cationic polyelectrolyte is partially neutralized with a mono and/or multivalent cation. Particularly good results are achieved if the anionic polyelectrolyte and/or amphoteric anionic polyelectrolyte in the mixture with cationic and/or amphoteric cationic polyelectrolyte is partially neutralized with alkaline metal cations and/or amines and/or alkanol amines and/or quaternary ammonium compounds, in particular however with $Na^+$ and/or $Ca^{2+}$ and/or $Mg^{2+}$.

The limit viscosity of the cationic and/or amphoteric cationic polyelectrolytes used in the aqueous suspension is preferably in the range between 9.2 ml/g and 48.5 ml/g, particularly preferably however in the range between 16.2 ml/g and 31.2 ml/g.

A further preferred embodiment of the process according to the invention is characterized by the following process steps:

a) an aqueous suspension of minerals and/or fillers and/or pigments is wet ground together with the dispersing and grinding agent mixture according to the invention, b) a part of the partially neutralized anionic and/or partially neutralized amphoteric anionic polyelectrolyte being added before the grinding and c) a part of the partially neutralized anionic and/or partially neutralized amphoteric anionic polyelectrolyte being added during the grinding and/or d) a part of the partially neutralized anionic and/or partially neutralized amphoteric anionic polyelectrolyte being added after the grinding, e) and the cationic and/or amphoteric cationic polyelectrolyte being added completely before the grinding or only f) a part of the cationic and/or amphoteric cationic polyelectrolyte being added before the grinding and g) a part of the cationic and/or amphoteric cationic polyelectrolyte being added during the grinding and/or h) a part of the cationic and/or amphoteric cationic polyelectrolyte being added after the grinding.

Particularly advantageous is a process in which a) 10-90% by weight of the partially neutralized aniinic and/or partially neutralized amphoteric anionic polyelectrolyte are added before the grinding and b) 10-90% by weight of the partially neutralized anionic and/or partially neutralized amphoteric anionic polyelectrolyte are added during the grinding and/or of the partially neutralized anionic c) 0-80% by weight of the partially neutralized anionic and/or partially neutralized amphoteric anionic polyelectrolyte are added after the grinding, d) 50-100% by weight of the cationic and/or cationic amphoteric polyelectrolyte are added before the grinding and e) 0-50% by weight of the cationic and/or cationic amphoteric polyelectrolyte are added during the grinding and/or f) 0-50% by weight of the cationic and/or amphoretic cationic polyelectrolyte are added after the grinding.

Good results are achieved if a process is used in which a) 20-40% by weight of the partially neutralized anionic and or partially neutralized amphoteric anionic polyelectrolyte are added before the grinding and b) 60-80% by weight of the partially neutralized anionic and/or partially neutralized amphoteric anionic polyelectrolyte are added during the grinding and/or c) 0-20% by weight of the partially neutralized anionic and/or partially neutralized amphoteric anionic polyelectrolyte are added after the grinding, d) 50-100% by weight of the cationic and/or cationic amphoteric polyelectrolyte are added before the grinding and e) 0-50% by weight of the cationic amphoteric polyelectrolyte are added during the grinding and/or f) 0-50% by weight of the cationic and/or amphoteric cationic polyelectrolyte are added after the grinding.

Very good results are achieved if a process is used in which a) 25-35% by weight of the partially neutralized anionic and/or partially neutralized amphoteric anionic polyelectrolyte are added before the grinding and b) 65-75% by weight of the partially neutralized anionic and/or partially neutralized amphoteric anionic polyelectrolyte are added during the grinding and/or c) 0-10% by weight of the partially neutralized anionic and/or partially neutralized amphoteric anionic polyelectrolyte are added after the grinding and d) 70-100% by weight of the cationic and/or cationic amphoteric polyelectrolyte are added before the grinding and e) 0-30% by weight of the cationic and/or cationic amphoteric polyelectrolyte are added during the grinding and/or f) 0-30% by weight of the cationic and/or amphoteric cationic polyelectrolyte are added after the grinding.

Excellent results are achieved in a process wherein a) 30% by weight of the partially neutralized anionic and/or partially neutralized amphoteric anionic polyelectrolyte are added before the grinding and b) 70% by weight of the partially neutralized anionic and/or partially neutralized amphoteric anionic polyelectrolyte are added during the grinding and c) 100% by weight of the cationic and/or cationic amphoteric polyelectrolyte are added before the grinding.

According to the invention, the aqueous suspension of minerals and/or fillers and/or pigments is used in paper manufacture or production. Further uses are the surface treatment (pigmenting of the paper surface in the size press of the papermaking machine), the use in paper coating apparatus, in the preliminary coat and in the top coat in paper coating, in the wood pulp for impurity control (pitch control), in the circulation water of the papermaking machine for COD reduction (chemical oxygen demand reduction), in the purification plant for waste water treatment, for preflocculating anionically stabilized pigment and/or mineral and/or filler suspensions in paper production or for preflocculating (immobilization of coating slips in the coating apparatus.

The invention has succeeded in preparing a mineral and/or filler and/or pigment suspension by grinding at high solid contents of ≧60% by weight in which the mineral and/or filler and/or pigment particles are stabilized both electrostatically positively and probably also sterically and the suspension remains viscosity-stable for weeks and for example the retention in papermaking is excellent.

A surprising and unpredictable fact is that with the suitable combination of one or more cationic polyelectrolytes and/or one or more amphoteric cationic polyelectrolytes and one or more partially neutralized anionic polyelectrolytes and/or one or more amphoteric anionic partially neutralized polyelectrolytes and the suitable addition point of the polyelectrolytes before, during and/or after the grinding process, under the high shearing forces and temperatures which occur in wet grinding no mutual neutralization of the oppositely charged polymers and thus coagulation of the polymers occurs. On the contrary, an optimum grinding and stabilizing of the suspension is effected in that the anionic polyelectrolytes according to the invention a) presumably act as bridge formers between the mineral and/or filler and/or pigment particles and the cationic and/or amphoteric cationic polyelectrolytes according to the invention, the cationic and/or amphoteric cationic polyelectrolyte thus fixed to the mineral and/or filler and/or pigment surface giving the mineral and/or filler and/or pigment particle a positive charge and thereby leading to an electrostatically positive stabilization of the system, and b) according to the invention by further additions of the anionic polyelectrolytes according to the invention during and/or after the grinding these presumably act as bridge formers between the cationic polymer chains of the cationic and/or amphoteric cationic polyelectrolyte, a superstructure probably being formed which sterically stabilizes the mineral and/or filler and/or pigment particles, leading to a substantially lower stable viscosity at high concentration than when the total amount of anionic polyelectrolyte according to the invention is added at the start of the grinding.

A fact which is surprising and likewise unpredictable is that the neutralization degree of the anionic polyelectrolytes according to the invention with mono and/or multivalent cations has a decisive influence on the storage stability of the mineral and/or filler and/or pigment suspension, i.e. on the viscosity constancy of the suspension with time.

When using anionic polyelectrolytes neutralized with 100 Mol. % sodium-neutralized anionic polyelectrolytes as used in the examples of EP 0278602 A1, the viscosity increases with time to such an extent that the suspension becomes useless.

In contrast, when using anionic polyelectrolytes and/or amphoteric anionic polyelectrolytes partially neutralized according to the invention with mono and/or multivalent cations the viscosity remains stable for days to weeks and proportional to the neutralization degree.

The lower the neutralization degree with monovalent cations the better the storage stability. Best suited are neutralization degrees of 5-10 Mol. %. Multivalent cations, such as calcium and/or magnesium, have a smaller negative influence on the storage stability.

With non-neutralized anionic polyelectrolytes, specifically with polyacrylic acid, the problem is encountered that a usually 40% by weight aqueous polymer solution is very highly viscous and normally has a crystallization temperature above 0° C. Polyacrylic acid crystallizes at 20° C. This leads to problems in the metering and dosing, in particular in cold times of the year and specifically in Scandinavia. This gives an irregular dosing which leads to great viscosity fluctuations in the mineral and/or filler and/or pigment suspensions to be made.

This is however not the case with the anionic polyelectrolytes according to the invention.

A good storage stability with regard to the viscosity and the sedimentation behaviour is of decisive importance above all in transport and with large storage tanks in order to prevent the material being spoilt. With the mineral and/or filler and/or pigment suspension prepared according to the invention it is possible to freely choose the production location (preparation location of the mineral and/or filler and/or pigment suspension) and the user location (e.g. paper mill). The production location can thus be adapted to the geological occurrences of the mineral and/or filler and/or pigment materials and there is no need to take account of the location of the customer for purely logistical reasons.

An aqueous suspension of minerals and/or fillers and/or pigments having a solid content ≧60% by weight, with respect to the dry minerals and/or fillers and/or pigments, is prepared according to the invention by grinding a coarsely broken crude rock, a combination of a partially neutralized anionic and/or partially neutralized amphoteric anionic polyelectrolyte and a cationic and/or amphoteric cationic polyelectrolyte being used in such a manner that the entire or part of the cationic and/or the amphoteric cationic polyelectrolyte and only a part of the partially neutralized anionic polyelectrolyte and/or of the partially neutralized amphoteric anionic polyelectrolyte is added at the beginning of the grinding and further parts of the anionic polyelectrolytes according to the invention are added during the grinding and/or after the grinding to reduce the viscosity.

Although the cationic and/or amphoteric cationic polyelectrolyte is present in excess and there is therefore a positive charge on the mineral and/or filler and/or pigment particles, further addition of the anionic and/or amphoteric anionic polyelectrolyte according to the invention during the grinding and/or after the grinding results in an enormous reduction of viscosity which was not predictable.

With the partial neutralization according to the invention of the anionic and/or amphoteric anionic polyelectrolyte with mono and/or multivalent cations, in addition a very stable viscosity for several weeks is obtained. This effect was not obtainable with any of the systems corresponding to the prior art.

In the examples according to the prior art the grinding had to be stopped before reaching the desired fineness because of blockage of the mill. The blockage of the mill was due to an enormous rise in viscosity during the grinding.

The viscosity rise is probably due to normally cationic polymeric polyelectrolytes reacting together with polymeric anionic polyelectrolytes to form salts and mutually neutralizing each other and precipitating.

With the polyelectrolyte combination according to the invention and the addition points according to the invention this surprisingly does not occur but on the contrary a pronounced reduction in viscosity which cannot be fully explained. The anionic and/or amphoteric anionic polyelectrolyte according to the invention added during the grinding and/or subsequently does not have a charge-neutralizing effect on the cationic and/or amphoteric cationic polyelectrolyte as was actually to be expected. The grain distribution, concentration and low viscosity of the mineral and/or filler and/or pigment suspensions ideal for the user, mainly the paper industry, can be achieved with the process according to the invention in one working operation, representing an enormous economical and qualitative advance.

Preferably, the concentration of the aqueous slurry is 60-70% by weight with respect to the dry mineral.

Preferably the raw material before the grinding process has according to the invention a mean equivalent spherical particle diameter of 10-50 μm (measured on the Sedigraph 5100).

Thus, in the grinding the anionic and/or amphoteric anionic polyelectrolyte according to the invention, which as regards its chemical properties is attached to the surface, newly formed in grinding, of the mineral and/or filler and/or pigment, presumably serves as bridge former between the mineral and/or filler and/or pigment and the cationic and/or amphoteric cationic polyelectrolyte. The thereby adequately fixed cationic and/or amphoteric cationic polyelectrolyte gives the mineral and/or filler and/or pigment particle a positive charge. In addition, the anionic and/or amphoteric anionic polyelectrolyte according to the invention added in the further steps to the mineral and/or filler and/or pigment suspension presumably acts with the chain length according to the invention as bridge former between the polymer chains of the cationic and/or amphoteric cationic polyelectrolyte, this leading to larger polymer chain structures which presumably additionally sterically stabilize the mineral particles.

In the grinding the cationic and/or amphoteric cationic polyelectrolyte which assisted by the anionic and/or amphoteric anionic polyelectrolyte according to the invention, is presumable attached to the mineral and/or filler and/or pigment surface, serves as positive charge carrier and thus positively stabilizes the mineral and/or filler and/or pigment particles.

In addition, the assumed bridge formation between the anionic and/or amphoteric polyelectrolyte according to the invention and the cationic and/or amphoteric cationic polyelectrolyte presumably effects a steric stabilization of the mineral and/or filler and/or pigment particles.

Suitable mixtures of the anionic and/or amphoteric anionic polyelectrolyte according to the invention and of the cationic and/or amphoteric cationic polyelectrolyte before grinding are, in accordance with the invention:

| partially neutralized anionic and/or partially neutralized amphoteric anionic polyelectrolyte to cationic and/or amphoteric cationic polyelectrolyte = 1:10 to 1:40 | |
|---|---|
| preferably for marble | 1:12 |
| for champagne chalk | 1:30 |

During and/after the grinding, depending on the concentration and desired end viscosity, partially neutralized anionic and/or partially neutralized amphoteric anionic polyelectrolyte is again added. The amount is preferably about twice as much as before the grinding.

Further Examples According to the Invention

Example 11

As in example 1a (prior art) but partially neutralized polyacrylic acid as in example 12.

| Viscosity in mPas | | |
|---|---|---|
| after 1 hr. | 1 day | 15 days |
| 144 | 152 | 280 |

Example 11 clearly shows that in contrast to example 1a (prior art) with a partially neutralized polyacrylic acid a substantially better storage stability for several weeks is achieved.

Example 12

A 70% by weight aqueous slurry of natural marble with a grain distribution such that 60% of the particles have an equivalent spherical diameter <2 μm (measured on the Sedigraph 5100) were dispersed with 0.33% by weight, with respect to the dry marble, of the following amphoteric cationic polymer (copolymer)

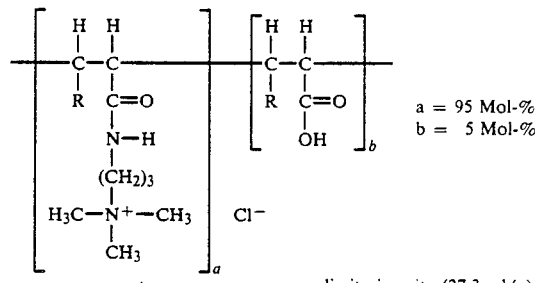

limit viscosity (27.3 ml/g)

and with 0.06% by weight, with respect to the dry marble, polyacrylic acid (10 Mol. of the carboxyl groups neutralized) partially neutralized with caustic soda of different specific viscosities or molecular weights with vigorous stirring (8000 rpm. Agitator blade diameter 50 mm). The objective of this test series was to determine the optimum specific viscosity or the molecular weight of the partially neutralized anionic polyelectrolyte.

| spec. viscosity of the partially neutralized polyacrylate | viscosity of the suspension |
|---|---|
| 0.2 | 2640 mPas |
| 0.35 | 370 mPas |
| 0.54 | 350 mPas |
| 0.71 | 1420 mPas |

The optimum specific viscosity of the partially neutralized polyacrylate is 0.35-0.54.

Example 13

A 67% by weight aqueous slurry of natural marble with a grain distribution such that 60% by weight of the particles have an equivalent spherical diameter <2 μm (measured on the Sedigraph 5100) were dispersed with 0.33% by weight, with respect to the dry marble, of the copolymer of example 12 but with different limit viscosities or molecular weights, and 0.06% by weight, with respect to the dry marble, of the partially neutralized polyacrylate of example 12 with the specific viscosity of 0.35 with vigorous stirring (8000 rpm agitator blade diameter 50 mm).

| Limit viscosity of the cationic copolymer | Viscosity of the suspension 1 hr. after the dispersion |
|---|---|
| 9.2 ml/g | 730 mPas |
| 12.8 ml/g | 500 mPas |
| 15.5 ml/g | 350 mPas |
| 16.2 ml/g | 156 mPas |
| 31.2 ml/g | 112 mPas |
| 48.5 ml/g | 840 mPas |

The optimum limit viscosity of the cationic polymer used is between 15 ml/g and 40 ml/g.

Example 14

A 70% by weight aqueous slurry of natural marble with a grain distribution such that 60% by weight of the particles have an equivalent spherical diameter <2 μm (measured on the Sedigraph 5100) were dispersed with 0.33% by weight, with respect to the dry marble, of the copolymer of example 12 and 0.06% by weight with respect to the dry marble, polyacrylic acid (spec. viscosity 0.35) with a different neutralization degree of the carboxyl groups with caustic soda with vigorous stirring (8000 rpm. Agitator blade diameter 50 mm).

| Neutralization degree of the carboxyl groups of the polyacrylic acid | Viscosity of the suspension | | | |
|---|---|---|---|---|
| | after 1 hr. | after 6 days | after 12 days | after 18 days |
| 100 Mol. % neutr. | 148 mPas | 640 mPas | 1560 mPas | >3000 mPas |
| 70 Mol. % neutr. | 128 mPas | 350 mPas | 1075 mPas | 1420 mPas |
| 50 Mol. % neutr. | 112 mPas | 176 mPas | 720 mPas | 1075 mPas |
| 30 Mol. % neutr. | 112 mPas | 172 mPas | 460 mPas | 720 mPas |
| 10 Mol. % neutr. | 112 mPas | 128 mPas | 172 mPas | 156 mPas |

The best long-time stability is achieved with a polyacrylic acid in which 5-10 Mol. % of the carboxyl groups are neutralized.

Example 15

A 70% by weight aqueous slurry of natural marble with a grain distribution such that 60% by weight of the particles have an equivalent spherical diameter of <2 μm (measured on the Sedigraph 5100) was dispersed with 0.33% by weight, with respect to the dry marble, of different percentage molar compositions of the copolymer of example 12 and 0.06% by weight with respect to the dry marble, of the partially neutralized polyacrylate (spec. viscosity 0.35, from example 12) with vigorous stirring (8000 rpm. Agitator blade diameter 50 mm).

| Mol. % cationic monomer | Mol. % anionic monomer | Viscosity of the suspension after 1 hr. |
|---|---|---|
| 80 Mol. % | 20 Mol. % | 680 mPas |
| 87 Mol. % | 13 Mol. % | 580 mPas |
| 95 Mol. % | 5 Mol. % | 172 mPas |
| 100 Mol. % | 0 Mol. % | 420 mPas |

The optimum monomer composition of the cationic polyelectrolyte is 95 Mol. % cationic compound and 5 Mol. % anionic compound.

Example 16

A 67% by weight aqueous slurry of natural marble having an equivalent spherical mean particle diameter of 12 μm (measured on the Sedigraph 5100) was ground with the following recipe in a Dynomill (0.6 l grinding container) using grinding bodies of glass φ 1 mm) to a grain distribution that 60% by weight of the particles had an equivalent spherical diameter <2 μm (measured on the Sedigraph 5100). spherical diameter <2 μm (measured on the Sedigraph 5100).

| | Recipe: |
|---|---|
| 5000 g | marble |
| 15 g | cationic copolymer corresponding to the formula of example 12 |
| 1.35 g | polyacrylic acid (spec. viscosity 0.54), 5 Mol. % of the carboxyl groups neutralized with NaOH, added before grinding |
| 3.15 g | polyacrylic acid (spec. viscosity 0.54), 5 Mol. % of the carboxyl groups neutralized with NaOH, added during the grinding |
| 2472 | water |

| Viscosity: | after 2 hrs. | 1 day | 5 days | 10 days | 20 days |
|---|---|---|---|---|---|
| | 200 | 116 | 148 mPas | 104 | 104 |

It is clearly apparent in example 16 that with the type and combination of anionic and cationic polyelectrolytes according to the invention a very low viscosity stable for many weeks can be achieved with even fine mineral and/or filler and/or pigment suspensions produced by grinding.

Example 17

A 67% by weight aqueous slurry of champagne chalk having an equivalent spherical mean particle diameter of 12 μm (measured on the Sedigraph 5100) was ground with the following recipe in a Dynomill (0.6 l grinding container) using grinding bodies of glass (φ 1 mm) to a grain distribution curve such that 67% by weight of the particles had an equivalent spherical diameter <2 μm (measured on the Sedigraph 5100).

| | Recipe: |
|---|---|
| 5000 g | champagne chalk |
| 25 g | cationic copolymer from example 12 |
| 0.5 g | polyacrylic acid (spec. viscosity 0.54) 5 Mol. % of the carboxyl groups neutralized with NaOH, added before the grinding |
| 2472 g | water |

Viscosity in mPas

| after 1 hr. | 1 day | 5 days | 10 days | 20 days |
|---|---|---|---|---|
| 2400 | 3900 | >5000 | | |

| 2.5 g | polyacrylic acid (spec. viscosity 0.54), 5 Mol. % of the carboxyl groups neutralized with NaOH, added 5 min. after the grinding with vigorous stirring (8000 rpm. Agitator blade diameter 50 mm) |
|---|---|

Viscosity in mPas

| after 1 hr. | 1 day | 5 days | 10 days | 20 days |
|---|---|---|---|---|

| -continued |
|---|
| Recipe: |
| 235 | 230 | 200 | 200 | 210 |

It is clearly apparent in example 17 that a subsequent addition of the anionic polyelectrolyte according to the invention also gives an enormous viscosity reduction and the viscosity remains stable for weeks.

Example 18

A 60% by weight aqueous slurry of natural marble having an equivalent spherical mean particle size of 12 μm (measured on the Sedigraph 5100) was ground with the following recipe in a Dynomill (0.6 l grinding container) using grinding bodies of glass (φ 1 mm) to a grain distribution curve such that 88% by weight of the particles had no equivalent spherical diameter <2 μm (measured on the Sedigraph 5100).

| Recipe: | |
|---|---|
| 5000 g | marble |
| 40 g | cationic copolymer from example 12 |
| 1.35 g | polyacrylic acid (spec. viscosity 0.54), 5 Mol. % of the carboxyl groups neutralized with NaOH, added before the grinding |
| 2.65 g | polyacrylic acid (spec. viscosity 0.54), 5 Mol. % of the carboxyl groups neutralized with NaOH, added during the grinding |
| 3363 g | water |

| Viscosity: | after 1 hr. | 1 day | 4 days | 8 days | 11 days |
|---|---|---|---|---|---|
| | 500 | 520 | 400 | 400 | 390 mPas |

Very high finenesses, as used in coating recipes, can also be made without any problems by grinding coarsely broken crude rock or stone at high concentrations.

Example 19

A 67% by weight aqueous slurry of natural champagne chalk having an equivalent spherical mean particle diameter of 18 μm (measured on the Sedigraph 5100) was ground with the following recipe in a Dynomill (0.6 l grinding container) using grinding bodies of glass (φ 1 mm) to a grain distribution curve such that 67% by weight of the particles have an equivalent spherical diameter <2 μm (measured on the Sedigraph 5100).

| Recipe: | |
|---|---|
| 5000 g | champagne chalk |
| 37.5 g | cationic copolymer from example 12 |
| 1.35 g | polyacrylic acid (spec. viscosity 0.54), 5 Mol. % of the carboxyl groups neutralized with NaOH added before the grinding |
| 7.65 g | polyacrylic acid (spec. viscosity 0.54), 5 Mol. % of the carboxyl groups neutralized with NaOH added during the grinding |
| 2486 g | water |

| Viscosity: | after 1 hr. | 1 day | 4 days | 7 days |
|---|---|---|---|---|
| | 212 | 170 | 132 | 124 mPas |

Example 20

On a pilot-plant scale the natural marble used in example 16 was ground in a vertically disposed Perlmill (Sussmeier with 180 l content) with grinding bodies of glass (φ 1-2 mm) to a grain distribution curve such that 63% by weight of the particles had an equivalent spherical diameter <2 μm (measured on the Sedigraph 5100) at a concentration of 67.6% by weight solid.

50 tonnes of this suspension were made in batches of about 600 kg.

| Recipe: | |
|---|---|
| 400 kg | marble |
| 1.4 kg | cationic copolymer from example 12 |
| 0.12 kg | polyacrylic acid (spec. viscosity 0.54), 5 Mol. % of the carboxyl groups neutralized with NaOH, added before the grinding, |
| 0.24 kg | polyacrylic acid (spec. viscosity 0.54) 5 Mol. % of the carboxyl groups neutralized with NaOH, added during the grinding |
| 197 kg | water |

The hourly throughput of the Perlmill was 500 l slurry/hour.

| Viscosity: | after 1 hr. | 1 day | 7 days | 14 days | 21 days |
|---|---|---|---|---|---|
| cP | 230 | 230 | 150 | 150 | 160 |

Example 21

On a pilot-plant scale the natural marble used in example 16 was ground in a vertically disposed Perlmill (Sussmeier with 180 l content) with grinding bodies of glass (φ 1-2 mm) to a grain distribution curve such that 70% by weight of the particles had an equivalent spherical diameter <2 μm (measured on the Sedigraph 5100) at a concentration of 70.6 by weight. 4 tonnes of this slurry were made in batches of about 600 kg.

| Recipe: | |
|---|---|
| 400 kg | marble |
| 2.0 kg | cationic copolymer from example 12 |
| 0.12 kg | polyacrylic acid (spec. viscosity 0.54), 5 Mol. % of the carboxyl groups neutralized with NaOH added befor the grinding |
| 0.36 kg | polyacrylic acid (spec. viscosity 0.54), 5 Mol. % of the carboxyl groups neutralized with NaOH, added during the grinding |
| 168 kg | water |

The hourly throughput was 500 l suspension/hour.

| Viscosity: | after 1 hr. | 1 day | 7 days | 14 days | 21 days |
|---|---|---|---|---|---|
| | 450 | 420 | 400 | 400 | 400 |

Example 22

A 70% by weight aqueous slurry of titanium dioxide having a grain distribution such that 94% by weight of the particles have an equivalent spherical diameter <2 μm (measured on the Sedigraph 5100) were dispersed under high shearing forces (8000 rpm, agitator blade diameter 50 mm).

| Recipe: | |
|---|---|
| 1500 g | TiO$_2$ |
| 7 g | cationic polymer from example 12 |
| 640 g | water added |

| | Viscosity in mPas | | | |
|---|---|---|---|---|
| after 1 hr. | 1 day | 10 days | 20 days |

| | | | |
|---|---|---|---|
| 275 | — | 300 | 290 |

Example 23

A 65% by weight aqueous slurry of titanium dioxide having a grain distribution such that 94% by weight of the particles have an equivalent spherical diameter <2 µm (measured on the Sedigraph 5100) were dispersed under high shearing forces (8000 rpm, agitator blade diameter 50 mm).

| Recipe: | |
|---|---|
| 1250 g | TiO$_2$ |
| 2 g | cationic polymer from example 2 |
| 675 g | water added |

| Viscosity in mPas | | | |
|---|---|---|---|
| after 1 hr. | 1 day | 10 days | 20 days |
| 350 | 370 | 400 | 420 |

Example 24

A 60% by weight aqueous slurry of natural CaSO$_4$ having a grain distribution such that 23% by weight of the particles have an equivalent spherical diameter <2 µm (measured on the Sedigraph 5100) were disposed under high shearing forces (8000 rpm, agitator blade diameter 50 mm).

| Recipe: | |
|---|---|
| 1000 g | CaSO$_4$ |
| 3.6 g | cationic polymer from example 12 |
| 670 g | water added |

| Viscosity in mPas | | | |
|---|---|---|---|
| after 1 hr. | 1 day | 10 days | 20 days |
| 350 | 390 | 400 | |

Example 25

A 63% by weight aqueous slurry of CaCO$_3$ (75.5% slurry of example 7A) and dry talc 47% by weight having an equivalent spherical diameter <2µm (measured on the Sedigraph 5100) were dispersed under high shearing forces (8000 rpm, agitator blade diameter 50 mm) such that a 1:1 mixture of talc/CaCO$_3$ results.

| Recipe: | |
|---|---|
| 670 g | slurry, 74.5% of example 7A |
| 549 g | dry talc 91% |
| 2.8 g | cationic polymer of example 12 |
| 594 g | water added |

| Viscosity in mPas | | |
|---|---|---|
| after 1 hr. | 1 day | 2 days |
| 450 | | 500 |

USE EXAMPLE

The marble slurries made in production examples 20+21 were investigated for their retention in papermaking in comparison with a marble slurry made today usually with anionic dispersing agents.

| Test conditions: | | |
|---|---|---|
| Material: | 80% birch sulfate 20% pine sulfate | grinding degree 23° SR |
| Retention aid: | | 0.05% polyacrylamide (limit viscosity 700 ml/g) |

Execution of the retention investigation according to Britt-jar, company Paper Research Material, SYRACUSE, U.S.A.:

1. 275 ml 2% fibre suspension (OD 3.63 g fibres) and 275 ml dist. water introduced into the Britt-jar;
2. Britt-jar agitator at 700 rpm;
3. add 25.4 ml 5% mineral and/or filler and/or pigment suspension;
4. after 20 sec. add corresponding amount of retention agent;
5. after a further 25 sec. open drain cock and allow 100 ml backwater to run off.
6. In the backwater the CaCO$_3$ content is determined complexometrically after digestion with HCl or by flame AAS. For other minerals and/or fillers and/or pigments the backwater is filtered via membrane filters, ashed at 600° C., brought via an alkaline melt digestion, for example with NaOH/KOH in a zirconium crucible, to a water-soluble form and determined by means of AAS in the acidified state. By taking account of the corresponding convertion factors the respective minerals and/or fillers and/or pigments can be deduced.
7. Via the incorporated amount of minerals and/or fillers and/or pigments per 100 ml and the amount of minerals and/or fillers and/or pigments per 100 ml determined in the backwater, the filler retention can be calculated.

| Results: | |
|---|---|
| Products: | Filler First-pass retention |
| Anionically stabilized slurry with 60% < 2 µm (0.15% sodium polyacrylate spec. visc. 0.35) | 41.1% |
| anionically stabilized slurry with 70% < 2 µm (0.3% sodium polyacrylate spec. viscosity 0.54) | 35.3% |
| slurry from preparation example 19 | 61.9% |
| slurry from preparation example 20 | 67.8% |

By using a marble suspension produced with the new preparation method according to the invention it is possible to increase the filler retention without impairing the paper formation and paper strength, representing an enormous advance in the development.

The aqueous suspensions according to the invention and the process according to the invention for their preparation have among others the following advantages:

In contrast to the processes known hitherto it is possible to prepare highly concentrated (>60% by weight) mineral and/or filler and/or pigment suspension by wet grinding from coarsely broken crude rock.

The suspensions have excellent storage stability with low viscosities.

In use there are for example great advantages with regard to filler retention in paper production.

The grinding and dispersion is possible under high grinding forces and at the boiling temperature of the water.

We claim:

1. An aqueous suspension containing a dispersed substance and a dispersing agent, said dispersed substance comprising one or more members selected from the group consisting of minerals, fillers and pigments, to achieve a solids content of $\geq 60\%$ by weight, and said dispersed substance carrying an external neutral or positive charge, and said dispersing agent comprising one or more members selected from the group consisting of:

amphoteric polyelectrolytes containing anionic and cationic monomer units, the number of negative charges in the anionic monomer units equaling the number of positive charges in the cationic monomer units;

cationic polyelectrolytes;

amphoteric cationic polyelectrolytes in which the non-neutral monomer units each carry a predominantly positive charge;

amphoteric anionic polyelectrolytes in which the non-neutral monomer units each carry a predominantly negative charge;

partially neutralized anionic polyelectrolytes; and partially neutralized amphoteric anionic polyelectrolytes in which the non-neutral monomer units each carry a predominantly negative charge, the dispersed substance carrying a neutral or positive charge to the outside.

2. An aqueous suspension in accordance with claim 1 in which said amphoteric polyelectrolytes further contain neutral monomer units.

3. An aqueous suspension in accordance with claim 1 in which said dispersing agent comprises one or more members selected from the group consisting of:

(a) one or more amphoteric polyelectrolytes;
   (b) a mixture of one or more amphoteric polyelectrolytes and one or more amphoteric cationic polyelectrolytes;
   (c) a mixture of one or more amphoteric polyelectrolytes and one or more amphoteric slightly cationic polyelectrolytes;
   (d) a mixture of one or more amphoteric polyelectrolytes, one or more amphoteric cationic polyelectrolytes and one or more amphoteric anionic polyelectrolytes;
   (e) a mixture of one or more amphoteric polyelectrolytes, one or more amphoteric slightly cationic polyelectrolytes and one or more amphoteric anionic polyelectrolytes;
   (f) a mixture of one or more amphoteric polyelectrolytes, one or more amphoteric cationic polyelectrolytes and one or more amphoteric slightly anionic polyelectrolytes;
   (g) a mixture of one or more amphoteric polyelectrolytes, one or more amphoteric slightly cationic polyelectrolytes and one or more amphoteric slightly anionic polyelectrolytes;
   (h) one or more amphoteric cationic polyelectrolytes;
   (i) one or more amphoteric slightly cationic polyelectrolytes;
   (j) a mixture of one or more amphoteric cationic polyelectrolytes and one or more amphoteric anionic polyelectrolytes;
   (k) a mixture of one or more amphoteric slightly cationic polyelectrolytes and one or more amphoteric anionic polyelectrolytes;
   (l) a mixture of one or more amphoteric cationic polyelectrolytes and one or more amphoteric slightly anionic polyelectrolytes;
   (m) a mixture of one or more amphoteric slightly cationic polyelectrolytes and one or more amphoteric slightly anionic polyelectrolytes;
   (n) a mixture of one or more amphoteric polyelectrolytes and one or more amphoteric slightly anionic polyelectrolytes;
   (o) one or more amphoteric slightly anionic polyelectrolytes; and
   (p) a mixture of one or more cationic polyelectrolytes and amphoteric slightly cationic polyelectrolytes;

one or more of the polyelectrolytes of the invention being partially neutralized and the dispersed substance carrying a charge neutral or positive to the outside.

4. An aqueous suspension in accordance with claim 1 in which:

the functional group generating the positive charge in said amphoteric, amphoteric cationic and amphoteric anionic polyelectrolytes is a substituent of an ethylenic main chain of said polyelectrolytes, and is comprised of a member selected from the group consisting of quaternary ammonium groups, carboxyl groups, sulfonic acid groups and acid phosphoric acid ester groups; and the functional group generating the negative charge in said amphoteric, amphoteric cationic and amphoteric anionic polyelectrolytes is bound to said main chain via a member selected from the group consisting of

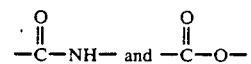

5. An aqueous suspension in accordance with claim 1 in which said amphoteric anionic, amphoteric and amphoteric cationic polyelectrolytes have the formula

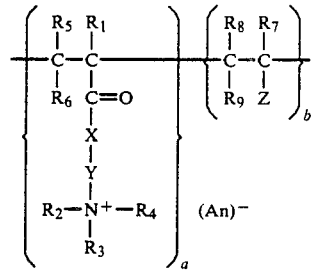

in which:

(An)⁻ is a member selected from the group consisting of chloride, bromide, iodide, $HSO_4^-$, $CH_3SO_4^-$ and nitrite;

$R_1$, $R_5$, $R_6$ and $R_7$ are independently members selected from the group consisting of H, alkyl and aryl;

$R_2$, $R_3$ and $R_4$ are independently members selected from the group consisting of alkyl and aryl;

$R_8$ and $R_9$ are independently members selected from the group consisting of H, alkyl and aryl when Z is other than $-CO_2H$, and from the group consisting of H, alkyl, aryl and $-CO_2H$ when Z is $-CO_2H$;

X is O or NH;
Y is $(CH_2)_n$ where n is 1 to 5;
Z is a member selected from the group consisting of

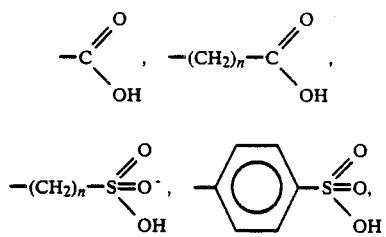

and an acidic phosphoric ester group, in which n is 1 to 18; and a and b represent the relative amounts of the respective monomers for which each appears as a subscript in the formula, such that the overall averaged mole ratio of a to b ranges from 5:95 to 99:1.

6. An aqueous suspension in accordance with claim 5 in which the substituent Z is partially neutralized by alkali or alkaline earth metal cations or a continuation thereof, the neutralization degree of Z being 1 to 99 mole percent.

7. An aqueous suspension in accordance with claim 6 in which the neutralization degree of Z with alkali metal cations is 1 to 25 mole percent.

8. An aqueous suspension in accordance with claim 5 in which Z is fully neutralized when the cation is selected from the group consisting of divalent ions, trivalent ions, $NH_4^+$, primary amines, secondary amines, tertiary amines and quaternary ammonium ions.

9. An aqueous suspension in accordance with claim 5 in which said substituent Z is non-neutralized.

10. An aqueous suspension in accordance with claim 5 in which, when $R_8$ and $R_9$ are other then

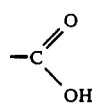

and when the amphoteric anionic polyelectrolytes are used in combination with the amphoteric cationic polyelectrolytes and the particles are thereby neutral or have positive surface charges, a and b are selected from the group consisting of the following, expressed in mole percents:

| amphoteric anionic: | amphoteric: | amphoteric cationic: |
|---|---|---|
| a = 5-49 | a = 50 | a = 51-99 |
| b = 51-95 | b = 50 | b = 49-1 |
| and | | |
| a = 47-49 | a = 50 | a = 51-80 |
| b = 51-53 | b = 50 | b = 49-20. |

11. An aqueous suspension in accordance with claim 5 in which the mole ratio of the anionic charge to the cationic charge is in the range of from 55:45 to 51:49.

12. An aqueous suspension in accordance with claim 1 in which said polyelectrolytes are compounds of the following formula:

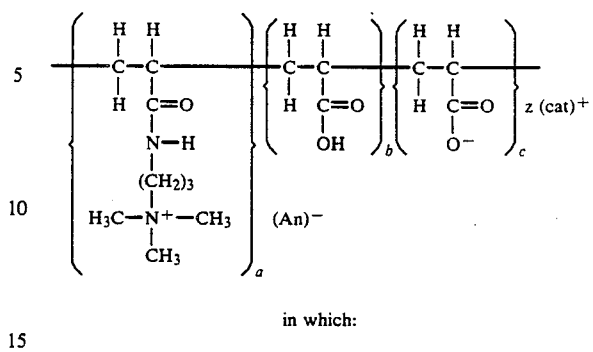

in which:

$$z = \frac{c}{\text{valency of (cat)}^+}$$

and if c=0, then z=0;

(cat)$^+$ is one or more members selected from the group consisting of alkali metal cation, alkaline earth metal cations and amines; and (An)$^-$ is a halide ion.

13. An aqueous suspension according to claim 12 in which a, b and c are present in the following mole percents:

| amphoteric anionic: | amphoteric: | amphoteric cationic: |
|---|---|---|
| a = 49-47 | a = 50 | a = 51-80 |
| b + c = 51-53 | b = 50 | b + c = 49-20. |

14. An aqueous suspension in accordance with claim 1 in which said polyelectrolytes other than any purely cationic polyelectrolytes have, upon neutralization with alkaline earth cations, an anionic component with a neutralization degree of 0.1 to 100 mole %.

15. An aqueous suspension in accordance with claim 1 in which the degree of neutralization of said amphoteric anionic, amphoteric neutral and amphoteric cationic polyelectrolytes, measured via the viscosity, lies int he range of 5 mPas to 150 mPas.

16. An aqueous suspension in accordance with claim 1 in which the dispersed substance and water together comprise 97.0% to 99.97% by weight, and the amphoteric polyelectrolyte comprises 0.03% to 3.0% by weight, of said aqueous suspension, with a solids content of 60% to 80% by weight based on the dry dispersed substance.

17. An aqueous suspension in accordance with claim 1 in which the dispersed substance is selected from one or more members of the group consisting of the second and third main group and the fourth subgroup of the Period Table of the Elements, calcium-containing, silicon-containing, aluminum-containing, titanium-containing dispersed substances, calcium carbonate, natural calcium carbonate, precipitated calcium carbonate, marble, chalk, dolomite, and dolomite-containing calcium carbonate.

18. An aqueous suspension in accordance with claim 1 in which the dispersing agent is a mixture of amphoteric cationic polyelectrolytes and amphoteric polyelectrolytes having the formula

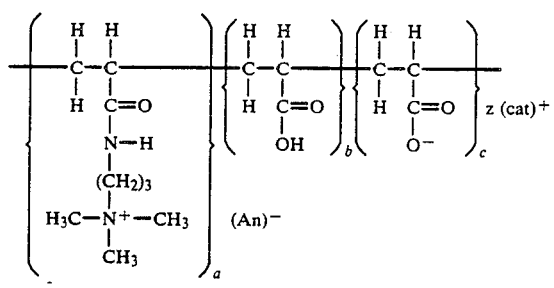

in which:

$$z = \frac{c}{\text{valency of (cat)}^+}$$

and if c=0, then z=0;

(cat)+ is one or more members selected from the group consisting of alkali metal cation, alkaline earth metal cations and amines;

(An)− is a halide ion; and a, b and c represent the relative amounts of the respective monomers for which each appears as a subscript in the formula, such that a, b and c are present in the following mole percents:

| amphoteric: | amphoteric cationic: |
|---|---|
| a = 50 | a = 70–99 |
| b + c = 50 | b = 30–1 |

19. An aqueous suspension in accordance with claim 1 in which the dispersing agent is a mixture of amphoteric slightly anionic polyelectrolyte and amphoteric cationic polyelectrolytes having the formula

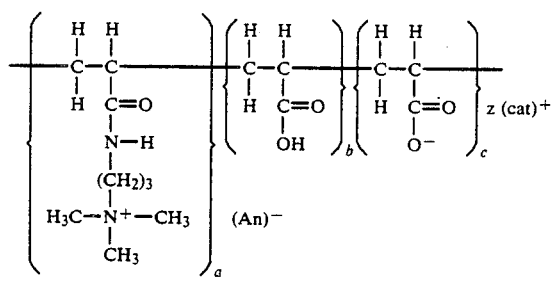

in which:

$$z = \frac{c}{\text{valency of (cat)}^+}$$

and if c=0, then z=0;

(cat)+ is one or more members selected from the group consisting of alkali metal cation, alkaline earth metal cations and amines;

(An)− is a halide ion; and a, b and c represent the relative amounts of the respective monomers for which each appears as a subscript in the formula, such that a, b and c are present in the following mole percents:

| amphoteric slightly anionic: | amphoteric cationic: |
|---|---|
| a = 47–49 | a = 70–99 |
| b + c = 51–53 | b = 30–1 |

20. An aqueous suspension in accordance with claim 1 in which the dispersing agent is a mixture of amphoteric cationic and amphoteric slightly cationic polyelectrolytes having the formula

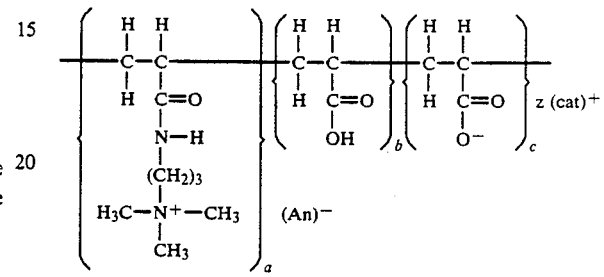

in which:

$$z = \frac{c}{\text{valency of (cat)}^+}$$

and if c=0, then z=0;

(cat)+ is one or more members selected from the group consisting of alkali metal cation, alkaline earth metal cations and amines;

(An)− is a halide ion; and a, b and c represent the relative amounts of the respective monomers for which each appears as a subscript in the formula, such that a, b and c are present in the following mole percents:

| amphoteric slightly cationic: | amphoteric cationic: |
|---|---|
| a = 51–53 | a = 80–97 |
| b + c = 49–47 | b = 20–3 |

21. A process for preparing an aqueous suspension containing a dispersed substance and a dispersing agent, said dispersed substance comprising one or more members selected from the group consisting of minerals, fillers and pigments, to achieve a solids content of ≧60% by weight, and said dispersing agent carrying an external neutral or positive charge, and said dispersing agent comprising one or more members selected from the group consisting of:

amphoteric polyelectrolytes containing anionic and cationic monomer units, the number of negative charges in the anionic monomer units equaling the number of positive charges in the cationic monomer units;

cationic polyelectrolytes;

amphoteric cationic polyelectrolytes in which the non-neutral monomer units each carry a predominantly positive charge;

amphoteric anionic polyelectrolytes in which the non-neutral monomer units each carry a predominantly negative charge;

partially neutralized anionic polyelectrolytes; and partially neutralized amphoteric anionic polyelectrolytes in which the non-neutral monomer units each carry a predominantly negative charge,
the dispersed substance carrying a neutral or positive charge to the outside;
said process comprising wet grinding an aqueous suspension of dispersed substance together with a dispersing and grinding agent mixture in such a manner that either:
  (a) said amphoteric polyelectrolytes are added completely before said grinding is begun, or
  (b) part of said amphoteric polyelectrolytes is added before said grinding is begun and the remainder added either during said grinding, after said grinding is terminated, or both during and after said grinding.

22. An aqueous suspension in accordance with claim 1 in which said dispersing agent comprises a mixture of
  (a) one or more members selected from the group consisting of cationic polyelectrolytes and amphoteric cationic polyelectrolytes in which the non-neutral monomer units carry predominantly positive charges; and
  (b) one or more members selected from the group consisting of partially neutralized anionic polyelectrolytes and partially neutralized amphoteric anionic polyelectrolytes in which the non-neutral monomer units carry predominantly negative charges.

23. An aqueous suspension in accordance with claim 22 in which the dispersing agent comprises a mixture of
  (a) one or more members selected from the group consisting of homopolymeric cationic polyelectrolytes and copolymeric amphoteric cationic polyelectrolytes in which the non-neutral monomer units carry predominantly positive charges; and
  (b) one or more members selected from the group consisting of homopolymeric partially neutralized anionic polyelectrolytes, copolymeric partially neutralized amphoteric anionic polyelectrolytes and amphoteric anionic partially neutralized polyelectrolytes in which the non-neutral monomer units carry predominantly negative charges.

24. An aqueous suspension in accordance with claim 22 in which, in said cationic polyelectrolytes and said amphoteric polyelectrolytes in which the non-neutral monomer units carry predominantly positive charges, the functional group generating the positive charge is in a substituent of the ethylenic main chain, the substituent being bound to the main chain via

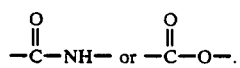

25. An aqueous suspension in accordance with claim 23 in which
the cationic polyelectrolyte contains quaternary ammonium groups and the amphoteric cationic polyelectrolytes contains groups selected from one or more members selected from the group consisting of quaternary ammonium groups, carboxyl groups, sulfonic acid groups, and acidic-phosphoric-acid-ester-containing groups;
the anionic partially neutralized and the amphoteric anionic partially neutralized polyelectrolyte each carry carboxyl groups; and
the anionic partially neutralized polyelectrolyte is one or more members selected from the group consisting of homo- and copolymer polyelectrolytes.

26. An aqueous suspension in accordance with claim 23 in which said cationic polyelectrolytes have the formula

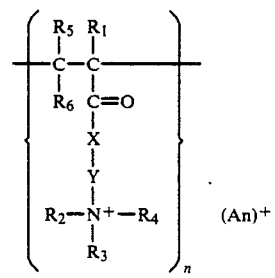

in which
(An)$^-$ is a member selected from the group consisting of chloride, bromide, iodide, HSO$_4^-$, CH$_3$SO$_4^-$ and nitrite;
R$_1$ is a member selected from the group consisting of H, alkyl and aryl;
R$_2$, R$_3$, R$_4$ and R$_6$ are members independently selected from the group consisting of alkyl and aryl;
R$_5$ is a member selected from the group consisting of H, alkyl, aryl and

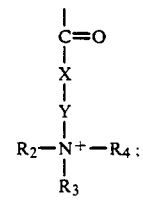

X is a member selected from the group consisting of O and N—H;
Y is a (CH$_2$)$_m$ where m=1 to 5; and
n is 20 and 3000.

27. An aqueous suspension in accordance with claim 22 in which said amphoteric cationic polyelectrolyte is a compound having the formula

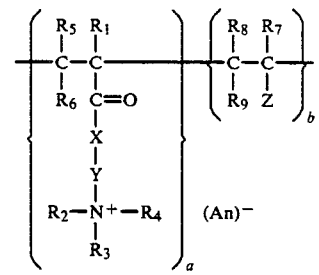

in which:
(An)$^-$ is a member selected from the group consisting of chloride, bromide, iodide, HSO$_4^-$, CH$_3$SO$_4^-$ and nitrite;
R$_1$, R$_5$, R$_6$ and R$_7$ are independently members selected from the group consisting of H, alkyl and aryl;

$R_2$, $R_3$ and $R_4$ are independently members selected from the group consisting of alkyl and aryl;

$R_8$ and $R_9$ are independently members selected from the group consisting of H, alkyl and aryl when Z is other than —$CO_2H$, and from the group consisting of H, alkyl, aryl and —$CO_2H$ when Z is —$CO_2H$;

X is O or NH;

Y is $(CH_2)_n$ where n is 1 to 5;

Z is a member selected from the group consisting of

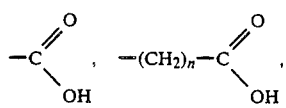

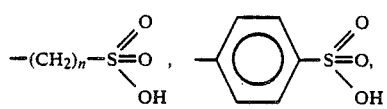

and an acidic phosphoric ester group, in which n is 1 to 18; and a and b represent the relative amounts of the respective monomers for which each appears as a subscript in the formula, such that the overall averaged mole ratio of a to b ranges from 5:95 to 99:1.

28. An aqueous suspension in accordance with claim 27 in which:

a = 70–99 mole %;
b = 1–30 mole %;
n = 1–18; and
(An)$^-$ is one or more members selected from the group consisting of chloride, bromide, iodide, $HSO_4^-$, $CH_3SO_4^-$ and nitrite.

29. An aqueous suspension in accordance with claim 27 in which, in said amphoteric anionic partially neutralized polyelectrolyte, a = 1–30 mole %; and
b = 70–99 mole %.

30. An aqueous suspension in accordance with claim 22 in which said anionic partially neutralized polyelectrolyte has the formula

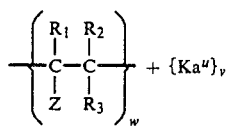

in which:

Z is one or more members selected from the group consisting of

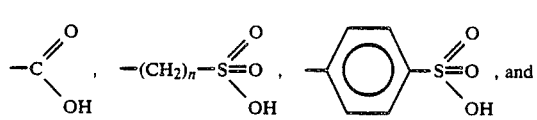

an acid phosphoric acid ester group;

$R_1$ is H or $CH_3$;

when Z is other than

$R_2$ and $R_3$ are members independently selected from the group consisting of H, alkyl and aryl;

when Z is

$R_2$ and $R_3$ are members independently selected from the group consisting of H, alkyl, aryl and

u is one or more members selected from the group consisting of +I, +II and +III;

Ka is one or more members selected from the group consisting of alkali, alkaline earth and earth metal ions;

w is 50 to 95 mole % per number Z in the monomer;

v is 5 to 41 mole % divided by u; and n is 1 to 12.

31. An aqueous suspension in accordance with claim 22 in which said dispersing agent is a mixture of (a) one or more members selected from the group consisting of (i) cationic polyelectrolytes have the formula

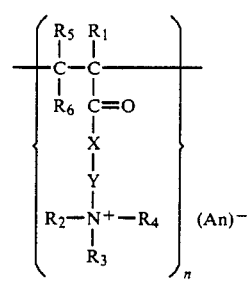

in which (An)$^-$ is a member selected from the group consisting of chloride, bromide, iodide, $HSO_4^-$, $CH_3SO_4^-$ and nitrite;

$R_1$ is a member selected from the group consisting of H, alkyl and aryl;

$R_2$, $R_3$, $R_4$ and $R_6$ are members independently selected from the group consisting of alkyl and aryl;

$R_5$ is a member selected from the group consisting of H, alkyl, aryl and

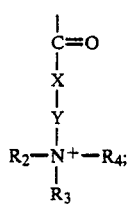

X is a member selected from the group consisting of O and N—H;
Y is a (CH$_2$)$_m$ where m=1 to 5; and
n is 20 to 3000;
and (ii) amphoteric cationic polyelectrolytes having the formula

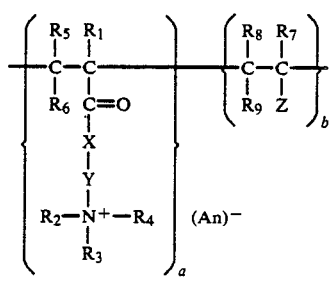

in which:
(An)$^-$ is a member selected from the group consisting of chloride, bromide, iodide, HSO$_4^-$, CH$_3$SO$_4^-$ and nitrite;
R$_1$, R$_5$, R$_6$ and R$_7$ are independently members selected from the group consisting of H, alkyl and aryl;
R$_2$, R$_3$, R$_4$ and R$_6$ are members independently selected from the group consisting of alkyl and aryl;
R$_8$ and R$_9$ are independently members selected from the group consisting of H, alkyl and aryl when Z is other than —CO$_2$H, and from the group consisting of H, alkyl, aryl and —CO$_2$H when Z is —CO$_2$H;
Z is O or NH;
Y is (CH$_2$)$_n$ where n is 1 to 5;
Z is a member selected from the group consisting of

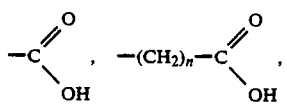

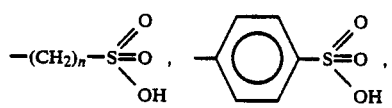

and an acidic phosphoric ester group, in which n is 1 to 18; and
a and b represent the relative amounts of the respective monomers for which each appears as a subscript in the formula, such that the overall averaged mole ratio of a to b ranges from 5:95 to 99:1; and (b) an anionic partially neutralized polyelectrolyte having the formula

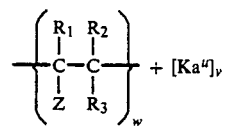

in which:
Z is one or more members selected from the group consisting of

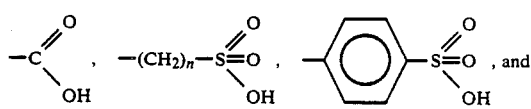

an acidic phosphoric acid ester group;
R$_1$ is H or CH$_3$;
when Z is other than

R$_2$ and R$_3$ are members independently selected from the group consisting of H, alkyl and aryl;
when Z is

R$_2$ and R$_3$ are members independently selected from the group consisting of H, alkyl, aryl and

u is one or more members selected from the group consisting of +I, +II and +III;
Ka is one or more members selected from the group consisting of alkali, alkaline earth and earth metal ions;
w is 50 to 95 mole % per number Z in the monomer;
v is 5 to 41 mole % divided by u; and
n is 1 to 12.

32. An aqueous suspension according to claim 22 in which said dispersing agent is a mixture according to the following general formula:

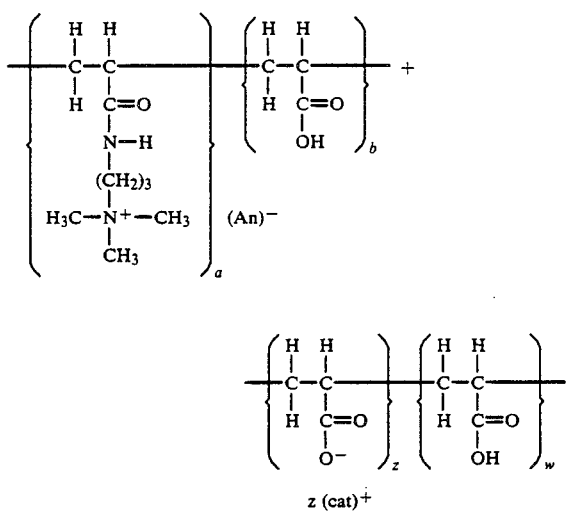

in which:

(cat)+ is one or more members selected from the group consisting of alkali and alkaline earth metal cations and amines;

(An)− is one or more members selected from the group consisting of chloride, bromide, iodide, $HOS_4^-$, $CH_3SO_4^-$ and nitrite;

a = 60–99 mole %;

b = 1–40 mole %;

z = 1–70 mole %; and w = 30–99 mole %.

33. An aqueous suspension in accordance with claim 22 in which:

1–70 mole % of the acid groups in component (b) of said mixture are neutralized, and the specific viscosity of component (b) of said mixture, measured in the full salt form, is between 0.2 and 1.0; and the polymerization degree of component (a) of said mixture, measured via the limiting viscosity, is from 5 mL/g to 50 mL/g.

34. An aqueous suspension in accordance with claim 22 in which said dispersed substance and water together comprise 97.0% to 99.89% by weight, said dispersing agent comprises 0.11% to 3.0% by weight, with a solids content corresponding to said dispersed substance on a dry basis comprising 60% to 80% by weight, of said aqueous suspension.

35. A process for preparing an aqueous suspension containing a dispersed substance and a dispersing agent, said dispersed substance comprising one or more members selected from the group consisting of minerals, fillers and pigments, to achieve a solids content of ≧60% by weight, and said dispersing agent carrying an external neutral or positive charge, and said dispersing agent comprising a mixture of the following components:

(a) one or more members selected from the group consisting of cationic polyelectrolytes and amphoteric cationic polyelectrolytes in which the non-neutral monomer units carry predominantly positive charges; and (b) one or more members selected from the group consisting of partially neutralized anionic polyelectrolytes and partially neutralized amphoteric anionic polyelectrolytes in which the non-neutral monomer units carry predominantly negative charges;

said process comprising wet grinding an aqueous suspension of said dispersed substance together with a dispersing and grinding agent mixture, in a procedure involving:

adding part of component (b) before said wet grinding is begun and the remainder either while said wet grinding is in progress, after said wet grinding is completed or both; and either adding all of component (a) before said wet grinding is begun, or adding part of component (a) before said wet grinding is begun and the remainder either while said wet grinding is in progress, after said wet grinding is completed or both.

* * * * *